United States Patent
Takayama et al.

(10) Patent No.: US 11,180,726 B2
(45) Date of Patent: Nov. 23, 2021

(54) CELL CULTURE APPARATUS AND CELL CULTURE METHOD

(71) Applicant: FUJIFILM CORPORATION, Tokyo (JP)

(72) Inventors: Hidetoshi Takayama, Kanagawa (JP); Shun Goto, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 181 days.

(21) Appl. No.: 16/503,473

(22) Filed: Jul. 4, 2019

(65) Prior Publication Data

US 2019/0322977 A1 Oct. 24, 2019

Related U.S. Application Data

(63) Continuation of application No. PCT/JP2018/001631, filed on Jan. 19, 2018.

(30) Foreign Application Priority Data

Jan. 20, 2017 (JP) .............................. JP2017-008911

(51) Int. Cl.
*C12M 3/00* (2006.01)
*C12M 1/00* (2006.01)
(Continued)

(52) U.S. Cl.
CPC ............ *C12M 41/32* (2013.01); *C12M 37/02* (2013.01); *C12M 41/46* (2013.01); *C12N 5/0696* (2013.01)

(58) Field of Classification Search
CPC ....... C12M 41/46; C12M 41/32; C12M 37/02
See application file for complete search history.

(56) References Cited

U.S. PATENT DOCUMENTS

2006/0019385 A1 1/2006 Smith et al.
2009/0181450 A1* 7/2009 Ribault ................... C12Q 1/24
435/287.1
(Continued)

FOREIGN PATENT DOCUMENTS

EP 0949526 A2 * 10/1999
EP 3249040 A1 11/2017
(Continued)

OTHER PUBLICATIONS

English translation of EP 0949526 to Andreas Stampfl, 1999, generated 2021.*

(Continued)

*Primary Examiner* — Nathan A Bowers
(74) *Attorney, Agent, or Firm* — Solaris Intellectual Property Group, PLLC

(57) ABSTRACT

Provided is a cell culture apparatus including a cell supply unit that supplies cells; a culture medium supply unit that supplies a culture medium; an additive supply unit that supplies an additive for inducing the differentiation of undifferentiated cells; a stirring unit that stirs a processing target; a separation unit that separates a component contained in the processing target; a culture vessel that cultures the cells; a first flow channel that forms a circulation route passing through the cell supply unit, the stirring unit, the separation unit, and the culture vessel; a second flow channel that connects the culture medium supply unit and the first flow channel; a third flow channel that connects the additive supply unit and the first flow channel; and a control unit that controls the feeding of liquid through the first flow channel, the second flow channel, and the third flow channel.

13 Claims, 13 Drawing Sheets

(51) Int. Cl.
  *C12M 1/34* (2006.01)
  *C12M 1/12* (2006.01)
  *C12N 5/074* (2010.01)

(56) References Cited

U.S. PATENT DOCUMENTS

| | | | |
|---|---|---|---|
| 2011/0275056 A1* | 11/2011 | Antwiler | C12M 41/32 |
| | | | 435/3 |
| 2012/0264210 A1* | 10/2012 | Bontinck | C12M 29/14 |
| | | | 435/366 |
| 2012/0294836 A1 | 11/2012 | Rowley et al. | |
| 2013/0345094 A1 | 12/2013 | Noggle et al. | |
| 2015/0072413 A1* | 3/2015 | Zenhausern | C12M 35/08 |
| | | | 435/347 |
| 2015/0166964 A1 | 6/2015 | Noggle et al. | |
| 2017/0306279 A1 | 10/2017 | Kagawa et al. | |

FOREIGN PATENT DOCUMENTS

| | | |
|---|---|---|
| JP | 2003-521877 A | 7/2003 |
| JP | 2007-312668 A | 12/2007 |
| JP | 2013-517771 A | 5/2013 |
| JP | 2015-502747 A | 1/2015 |
| JP | 2015-100309 A | 6/2015 |
| JP | 2016-529897 A | 9/2016 |
| WO | 00/46354 A1 | 8/2000 |
| WO | 2006/117925 A1 | 11/2006 |
| WO | 2013/187359 A1 | 12/2013 |
| WO | 2015/023658 A2 | 2/2015 |
| WO | 2016/117615 A1 | 7/2016 |
| WO | 2017/038887 A1 | 3/2017 |
| WO | 2017/040548 A1 | 3/2017 |

OTHER PUBLICATIONS

English translation of JP 2007312668 to Ieshima et al, 2007, generated 2021.*
Extended European Search Report dated Dec. 13, 2019, issued in corresponding EP Patent Application No. 18741731.6.
English language translation of the following: Office action dated Jul. 14, 2020 from the JPO in a Japanese patent application No. 2018-562460 corresponding to the instant patent application.
International Search Report issued in International Application No. PCT/JP2018/001631 dated Apr. 24, 2018.
Written Opinion of the ISA issued in International Application No. PCT/JP2018/001631 dated Apr. 24, 2018.
English language translation of the following: Office action dated Jan. 26, 2021 from the JPO in a Japanese patent application No. 2018-562460 corresponding to the instant patent application.

* cited by examiner

ADDITION OF FIRST ADDITIVE

CULTURE MEDIUM EXCHANGE [1]

RE-ADDITION OF FIRST ADDITIVE

CULTURE MEDIUM EXCHANGE [2]

ADDITION OF SECOND ADDITIVE

CULTURE MEDIUM EXCHANGE [3]

CULTURE MEDIUM EXCHANGE [4]

CELL CULTURE APPARATUS AND CELL CULTURE METHOD

CROSS-REFERENCE TO RELATED APPLICATIONS

This application is a continuation application of International Application No. PCT/JP2018/001631, filed Jan. 19, 2018, the disclosure of which is incorporated herein by reference in its entirety. Further, this application claims priority from Japanese Patent Application No. 2017-008911, filed Jan. 20, 2017, the disclosure of which is incorporated herein by reference in its entirety.

BACKGROUND

1. Technical Field

The disclosed technology relates to a cell culture apparatus and a cell culture method.

2. Related Art

For example, the following techniques are known as techniques relating to a cell culture apparatus that carries out processing relating to cell culture.

For example, JP2015-100309A discloses a cell management system comprising an automatic culture system having an automatic culture apparatus for automatically culturing cells and a cell management unit for managing information on the state of the cultured cells, a memory unit for storing the state of the cells cultured by the automatic culture apparatus, and an external computer installed under the orderer.

WO2013/187359A discloses a cell culture apparatus comprising a cylindrical culture tank; a support standing upright from a center of an inner surface of a bottom of the culture tank; and a stirring blade having an attaching portion mounted, rotatably relative to the support, on the upper part of the support, the upper part of which is secured to the attaching portion, that rotates with the support as the rotation center.

JP2016-529897A discloses an automated method for culturing stem cells using a robotic liquid processing system that includes a translational bed and a mobile multi-channel pipette.

SUMMARY

In a case of applying pluripotent stem cells such as embryonic stem cells (ES cells) or induced pluripotent stem cells (iPS cells) to regenerative medicine use or drug discovery support use, it is necessary to induce differentiation to produce desired cells from pluripotent stem cells. A method of applying chemical or physical stimulation to pluripotent stem cells can be mentioned as a method for the induction of differentiation. Further, in vivo, differentiated cells develop from any of three germ layers called ectoderm, mesoderm, and endoderm. In a case where differentiated cells are obtained from pluripotent stem cells following this, induction of differentiation into germ layers is carried out as a first step.

There has been no example proposed so far for a cell culture apparatus which has been able to produce a large amount of differentiated cells by continuously carrying out the series of processes required for the induction of differentiation as described above in a closed system, and it has been considered difficult to increase a culture scale of differentiated cells. In addition, in human-mediated culture techniques, the risk of biological contamination is increased, and the homogeneity of cells obtained by the culture may be reduced.

The disclosed technology has been made in view of the above-mentioned points and an object thereof is to make it possible to continuously carry out a series of processes required for inducing the differentiation of pluripotent stem cells in a closed system.

A cell culture apparatus according to the disclosed technology comprises:

a cell supply unit that supplies cells;

a culture medium supply unit that supplies a culture medium;

an additive supply unit that supplies an additive for inducing the differentiation of undifferentiated cells;

a stirring unit that stirs a processing target;

a separation unit that separates a component contained in the processing target;

a culture vessel that cultures the cells;

a first flow channel that forms a circulation route passing through the cell supply unit, the stirring unit, the separation unit, and the culture vessel;

a second flow channel that connects the culture medium supply unit and the first flow channel;

a third flow channel that connects the additive supply unit and the first flow channel; and a control unit that controls the feeding of liquid through the first flow channel, the second flow channel, and the third flow channel.

The separation unit may have at least one of a first filter membrane that carries out membrane separation of the undifferentiated cells from dead cells; a second filter membrane that carries out membrane separation of intermediates prior to the differentiation of the undifferentiated cells into differentiated cells from the undifferentiated cells; or a third filter membrane that carries out membrane separation of the intermediates from the differentiated cells.

The separation unit may have a plurality of filter membranes including at least two of the first filter membrane, the second filter membrane, and the third filter membrane, and in this case, the control unit may carry out control of selectively passing a cell suspension containing the cells through any of the plurality of filter membranes.

Sizes of openings provided in the membrane surfaces of the first filter membrane, the second filter membrane, and the third filter membrane may be different from one another.

It is preferred that the control unit carries out control of the feeding of liquid for applying a shear stress to a mixture of the additive and the culture medium, and then combining a cell suspension containing the cells and the mixture and transferring the combined mixture to the stirring unit.

The cell culture apparatus may further comprise a storage container provided between the cell supply unit and the stirring unit in the middle of the first flow channel. In this case, the control unit may carry out control of circulating the mixture between the storage container and the stirring unit to apply a shear stress to the mixture, and then combining the cell suspension and the mixture in the storage container and transferring the combined mixture to the stirring unit. In addition, the control unit may carry out control of flowing the mixture into a pipe to apply a shear stress to the mixture, and then combining the cell suspension and the mixture in the storage container and transferring the combined mixture to the stirring unit.

The control unit may continuously carry out the feeding of liquid for applying a shear stress to the mixture until the viscosity of the mixture reaches a predetermined viscosity.

The additive supply unit may include a first additive supply unit that supplies a first additive containing a Wnt signaling activator, and a second additive supply unit that supplies a second additive containing a Wnt signaling inhibitor.

The cell culture apparatus may further comprise an incubator that accommodates the culture vessel and keeps an ambient temperature of the culture vessel constant and a temperature gradient-reducing mechanism that reduces a temperature gradient generated along the first flow channel due to a temperature difference between the inside and the outside of the incubator.

The cell culture method according to the disclosed technology is a cell culture method for culturing a cell using the foregoing cell culture apparatus, in which the control unit carries out control of transferring a mixture containing the cell supplied from the culture medium supply unit, the additive supplied from the additive supply unit, and the culture medium supplied from the culture medium supply unit to the culture vessel through the stirring unit and the separation unit.

According to the disclosed technology, it is possible to continuously carry out a series of processes required for inducing the differentiation of pluripotent stem cells in a closed system.

BRIEF DESCRIPTION OF THE DRAWINGS

Exemplary embodiments according to the technique of the present disclosure will be described in detail based on the following figures, wherein.

DETAILED DESCRIPTION

Figure 1:
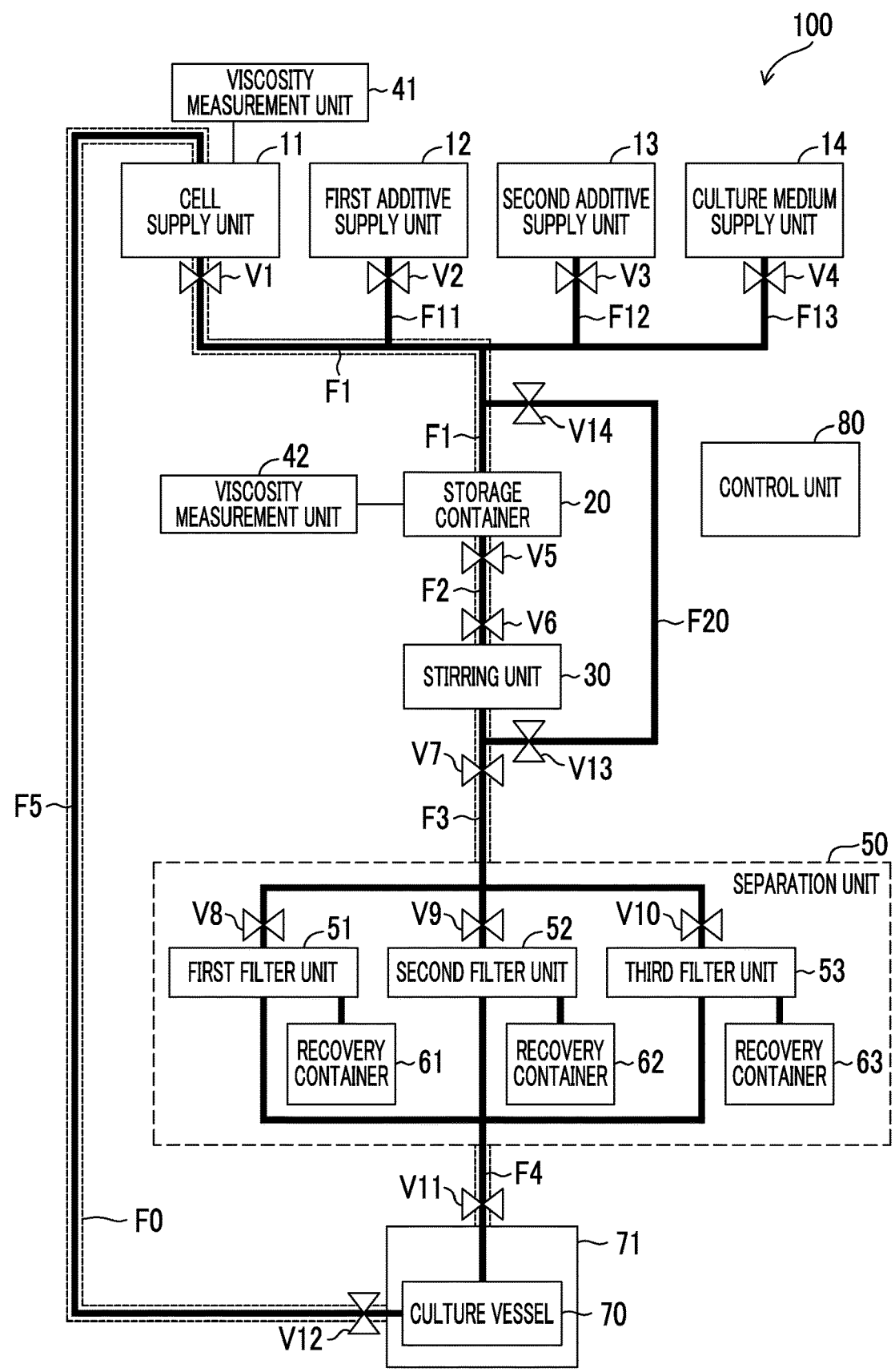
FIG. 1 is a block diagram showing a configuration of a cell culture apparatus according to an embodiment of the disclosed technology.

Hereinafter, an example of an embodiment of the disclosed technology will be described with reference to the drawings. In the drawings, the same or equivalent components and parts are denoted by the same reference numerals.

First Embodiment

FIG. 1 is a block diagram showing an example of a configuration of a cell culture apparatus 100 according to the embodiment of the disclosed technology. The cell culture apparatus 100 is a cell culture apparatus that automatically carries out a plurality of processes required to induce the differentiation of pluripotent stem cells into differentiated cells to produce desired differentiated cells.

Pluripotent stem cells are cells having a self-replication ability and a multilineage potential capable of differentiating into any of ectoderm, mesoderm, and endoderm. Examples of pluripotent stem cells include embryonic stem cells (ES cells), induced pluripotent stem cells (iPS cells), embryonic germ cells (EG cells), embryonal carcinoma cells (EC cells), multipotent adult progenitor cells (MAP cells), adult pluripotent stem cells (APS cells), and Muse cells (multilineage differentiating stress enduring cells). Differentiated cells are cells which have specific morphology and function following the differentiation of pluripotent stem cells. The differentiated cells produced using the cell culture apparatus 100 according to the present embodiment are not particularly limited, and examples thereof include cardiomyocytes and nerve cells.

The cell culture apparatus 100 comprises a cell supply unit 11, a first additive supply unit 12, a second additive supply unit 13, and a culture medium supply unit 14. The cell culture apparatus 100 further comprises a storage container 20, a stirring unit 30, viscosity measurement units 41 and 42, a separation unit 50, a culture vessel 70, and a control unit 80.

The cell supply unit 11 supplies a cell suspension containing the cells cultured in the cell culture apparatus 100 into a flow channel of the cell culture apparatus 100. An on-off valve V1 is provided in the vicinity of the outlet of the cell supply unit 11. The on-off valve V1 is controlled to be in an open state in a case of supplying the cell suspension from the cell supply unit 11, and is controlled to be in a closed state otherwise.

The first additive supply unit 12 supplies a first additive containing a Wnt signaling activator, which is necessary for inducing the differentiation of pluripotent stem cells, into the flow channel of the cell culture apparatus 100. An on-off valve V2 is provided in the vicinity of the outlet of the first additive supply unit 12. The on-off valve V2 is controlled to be in an open state in a case of supplying the first additive from the first additive supply unit 12, and is controlled to be in a closed state otherwise.

The second additive supply unit 13 supplies a second additive containing a Wnt signaling inhibitor, which is necessary for inducing the differentiation of pluripotent stem cells, into the flow channel of the cell culture apparatus 100. An on-off valve V3 is provided in the vicinity of the outlet of the second additive supply unit 13. The on-off valve V3 is controlled to be in an open state in a case of supplying the second additive from the second additive supply unit 13, and is controlled to be in a closed state otherwise.

The culture medium supply unit 14 supplies a fresh culture medium (culture fluid) used for the culture of cells into the flow channel of the cell culture apparatus 100. An on-off valve V4 is provided in the vicinity of the outlet of the culture medium supply unit 14. The on-off valve V4 is controlled to be in an open state in a case of supplying the culture medium from the culture medium supply unit 14, and is controlled to be in a closed state otherwise.

The storage container 20 is a container for temporarily storing the cell suspension supplied from the cell supply unit 11, the first additive supplied from the first additive supply unit 12, the second additive supplied from the second additive supply unit 13, and the culture medium supplied from the culture medium supply unit 14. The form of the storage container 20 is not particularly limited. For example, it is possible to use a container in the form of a glass or stainless steel container, or a plastic bag.

The stirring unit 30 is a processing unit that carries out a process of stirring and mixing the processing target flowing in through the flow channel F2. The stirring unit 30 preferably has a configuration as a static mixer having no drive unit. For example, the stirring unit 30 can be configured to include a tubular body, and a stirring element fixedly installed inside the tubular body and forming a spiral flow channel inside the tubular body. In addition, the stirring unit 30 may carry out stirring and mixing the processing target by rotationally driving a stirring blade.

The separation unit 50 is a processing unit that carries out a process of separating components contained in the processing target (cell suspension) flowing in through the flow channel F3. The separation unit 50 is configured to include a first filter unit 51, a second filter unit 52, and a third filter unit 53. Each of the first filter unit 51, the second filter unit 52, and the third filter unit 53 comprises filter membranes having different sizes of openings formed on the membrane surface through which the cell suspension passes. That is, the opening size of the filter membrane comprised in the first filter unit 51 is the smallest, and the opening size of the filter membrane comprised in the third filter unit 53 is the largest. The opening size of the filter membrane comprised in the second filter unit 52 is larger than the opening size of the filter membrane comprised in the first filter unit 51 and smaller than the opening size of the filter membrane comprised in the third filter unit 53. Each of the first filter unit 51, the second filter unit 52, and the third filter unit 53 carries out a membrane separation process with a filter membrane on the processing target (cell suspension) flowing in through the flow channel F3.

The first filter unit 51 is used at an early stage of culture before pluripotent stem cells start to differentiate. The first filter unit 51 has a filter membrane of an opening size suitable for membrane separation of living undifferentiated cells from dead cells. In the pluripotent stem cells, living undifferentiated cells form a cell mass which is an aggregate of multiple cells, and dead cells leave the cell mass to become single cells. Therefore, it is possible to separate living undifferentiated cells from dead cells by the membrane separation process. The first filter unit 51 is used for the purpose of removing dead cells from a cell suspension containing the living undifferentiated cells (cell mass) and the dead cells, and leaving the undifferentiated cells.

The second filter unit 52 is used at a stage where the pluripotent stem cells are differentiated into intermediates (ectoderm, mesoderm, and endoderm) prior to differentiation into differentiated cells such as cardiomyocytes. The second filter unit 52 has a filter membrane of an opening size suitable for membrane separation of undifferentiated cells that do not differentiate into intermediates from the intermediates. Since the size of the intermediates is larger than the size of the undifferentiated cells, it is possible to separate the undifferentiated cells from the intermediates by the membrane separation process. The second filter unit 52 is used for the purpose of removing undifferentiated cells from a cell suspension containing the undifferentiated cells and the intermediates and leaving the intermediates.

The third filter unit 53 is used at a stage where pluripotent stem cells are differentiated into differentiated cells such as cardiomyocytes. The third filter unit 53 has a filter membrane of an opening size suitable for membrane separation of intermediates which do not undergo a transition into differentiated cells, from the differentiated cells. Since the size of differentiated cells such as cardiomyocytes is larger than the size of intermediates such as ectoderm, mesoderm, and endoderm, it is possible to separate the differentiated cells from the intermediates by the membrane separation process. The third filter unit 53 is used for the purpose of removing the intermediates from a cell suspension containing the differentiated cells and the intermediates, and leaving the differentiated cells.

Each of the first filter unit 51, the second filter unit 52, and the third filter unit 53 may have a configuration of a tangential flow filter in which a processing target (cell suspension) flows along the membrane surface of the filter membrane. In addition, each of the first filter unit 51, the second filter unit 52, and the third filter unit 53 may have a configuration of a dead end flow filter in which the flow direction of the processing target (cell suspension) crosses the membrane surface of the filter membrane.

Recovery containers 61, 62, and 63 are connected to the first filter unit 51, the second filter unit 52, and the third filter unit 53, respectively. In the first filter unit 51, the second filter unit 52, and the third filter unit 53, the filtrates that have passed through the filter membranes are recovered in the recovery containers 61, 62, and 63, respectively.

In the cell culture apparatus 100 according to the present embodiment, the first filter unit 51, the second filter unit 52, and the third filter unit 53 are selectively used at a predetermined timing during the culture period. That is, the processing target (cell suspension) flowing into the separation unit 50 through the flow channel F3 passes through any one of the filter membranes of the first filter unit 51, the second filter unit 52, and the third filter unit 53.

On-off valves V8, V9, and V10 are provided in the vicinity of the inlets of the first filter unit 51, the second filter unit 52, and the third filter unit 53, respectively. The on-off valve V8 is controlled to be in an open state in a case of carrying out the membrane separation process by the first filter unit 51, and is controlled to be in a closed state otherwise. The on-off valve V9 is controlled to be in an open state in a case of carrying out the membrane separation process by the second filter unit 52, and is controlled to be in a closed state otherwise. The on-off valve V10 is controlled to be in an open state in a case of carrying out the membrane separation process by the third filter unit 53, and is controlled to be in a closed state otherwise.

Here, Table 1 below illustrates a preferred opening size of the filter membrane of each filter unit and the transfer destination after membrane separation in a case where dead cells (single cells) (up to 20 μm), aggregates (50 to 150 μm) of iPS cells which are an example of undifferentiated cells, aggregates (500 to 600 μm) of mesoderm which is an example of intermediates, and aggregates (200 to 300 μm) of cardiomyocytes which are an example of differentiated cells, which occur in cell culture for the induction of differentiation, are subjected to membrane separation in the first filter unit 51, the second filter unit 52, and the third filter unit 53.

culture vessel 70 and the inlet of the cell supply unit 11. The circulation flow channel F0 is an example of the first flow channel in the disclosed technology.

The first additive supply unit 12 is connected to the circulation flow channel F0 (flow channel F1) through a flow channel F11, and the second additive supply unit 13 is connected to the circulation flow channel F0 (flow channel F1) through a flow channel F12. The culture medium supply unit 14 is connected to the circulation flow channel F0 (flow channel F1) through a flow channel F13. The flow channel F13 is an example of the second flow channel in the disclosed technology. The flow channels F11 and F12 are examples of the third flow channel in the disclosed technology.

TABLE 1

| Range of preferred opening size d of filter membrane | | First filter unit 20 < d < 50 [μm] | Second filter unit 150 < d < 200 [μm] | Third filter unit 300 < d < 500 [μm] |
|---|---|---|---|---|
| Dead cells | Up to 20 μm | Into recovery container (permeation side) | Into recovery container (permeation side) | |
| Undifferentiated cells (aggregates of undifferentiated iPS cells) | 50 to 150 μm | Into culture vessel (blocking side) | | |
| Intermediates (aggregates of mesoderm) | 500 to 600 μm | | Into culture vessel (blocking side) | Into recovery container (permeation side) |
| Differentiated cells (aggregates of cardiomyocytes) | 200 to 300 μm | | | Into culture vessel (blocking side) |

A more preferred opening size of the filter membrane of the first filter unit 51 is 30 μm; a more preferred opening size of the filter membrane of the second filter unit 52 is 170 μm; and a more preferred opening size of the filter membrane of the third filter unit 53 is 400 μm.

The culture vessel 70 is a container for culturing cells. The form of the culture vessel 70 is not particularly limited. For example, a container having a form of a glass or stainless steel container or a plastic bag can be used. The culture vessel 70 is accommodated in, for example, an incubator 71 which is sealed and controlled at a temperature of 30° C. to 40° C. (preferably 37° C.) and a $CO_2$ concentration of 2% to 10% (preferably 5%).

The viscosity measurement unit 41 measures the viscosity of the cell suspension accommodated in the cell supply unit 11 and notifies the measurement results to the control unit 80. Similarly, the viscosity measurement unit 42 measures the viscosity of the liquid accommodated in the storage container 20 and notifies the measurement results to the control unit 80.

The cell culture apparatus 100 according to the present embodiment has a circulation flow channel F0 that forms a circulation route through the cell supply unit 11, the storage container 20, the stirring unit 30, the separation unit 50, and the culture vessel 70 in this order. The circulation flow channel F0 is configured to include flow channels F1, F2, F3, F4, and F5. The flow channel F1 is a flow channel that connects the outlet of the cell supply unit 11 and the inlet of the storage container 20. The flow channel F2 is a flow channel that connects the outlet of the storage container 20 and the inlet of the stirring unit 30. The flow channel F3 is a flow channel that connects the outlet of the stirring unit 30 and the inlet of the separation unit 50. The flow channel F4 is a flow channel that connects the outlet of the separation unit 50 and the inlet of the culture vessel 70. The flow channel F5 is a flow channel that connects the outlet of the The flow channel F2 provided between the storage container 20 and the stirring unit 30 is provided with on-off valves V5 and V6. The on-off valves V5 and V6 are controlled to be in an open state in a case of carrying out the feeding of liquid from the storage container 20 toward the stirring unit 30, and are controlled to be in a closed state otherwise.

Further, an on-off valve V7 is provided in the flow channel F3 provided between the stirring unit 30 and the separation unit 50. The on-off valve V7 is controlled to be in an open state in a case of carrying out the feeding of liquid from the stirring unit 30 toward the separation unit 50, and is controlled to be in a closed state otherwise.

The cell culture apparatus 100 has a flow channel F20 that directly connects the outlet of the stirring unit 30 and the inlet of the storage container 20. That is, one end of the flow channel F20 is connected to the flow channel F1, and the other end of the flow channel F20 is connected to the flow channel F3. The flow channel F20 is provided with on-off valves V13 and V14. The on-off valves V13 and V14 are controlled to be in an open state in a case of carrying out the feeding of liquid from the stirring unit 30 toward the storage container 20, and are controlled to be in a closed state otherwise.

The cell culture apparatus 100 comprises a plurality of pumps (not shown) that carry out the feeding of liquid through the flow channels F1 to F5, F11, F12, and F20. By adjusting the pressure of the inside of each of the cell supply unit 11, the first additive supply unit 12, the second additive supply unit 13, the culture medium supply unit 14, the storage container 20, the stirring unit 30, the separation unit 50, and the culture vessel 70, the feeding of liquid may be carried out between these individual elements.

The control unit 80 controls the feeding of liquid through the flow channels F1 to F5, F11, F12, and F20 by carrying out opening/closing control of the on-off valves V1 to V14 and drive control of the pumps (not shown).

The process for inducing the differentiation of pluripotent stem cells carried out in the cell culture apparatus 100 according to the present embodiment includes a first step of culturing pluripotent stem cells in a culture medium containing a Wnt signaling activator, and a second step of culturing the cells obtained in the first step in a culture medium containing a Wnt signaling inhibitor. The details of the method of differentiation induction including the above-mentioned first step and second step are described, for example, in WO2013/111875A.

Figure 2:
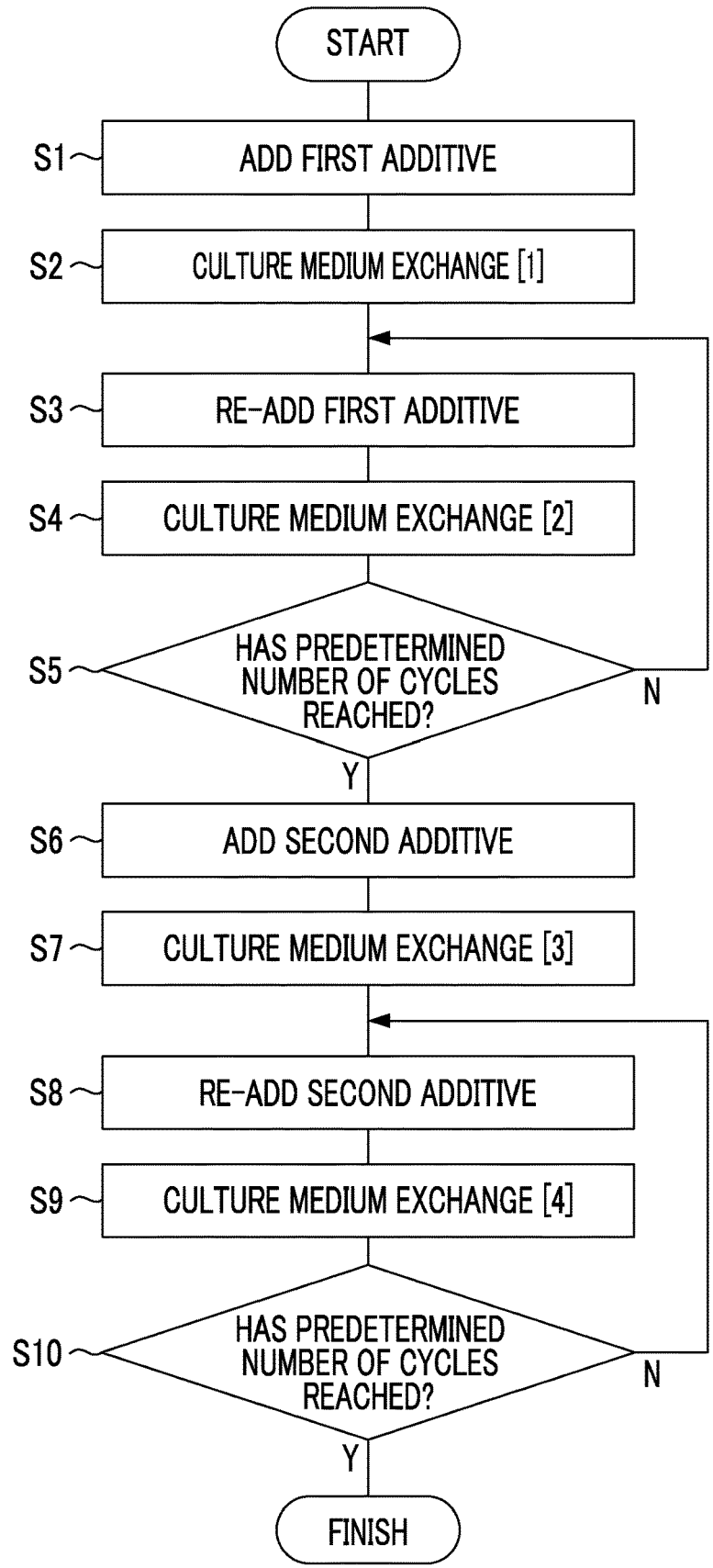
FIG. 2 is a flow chart showing an example of a processing flow for inducing the differentiation of pluripotent stem cells, which is carried out in the cell culture apparatus according to an embodiment of the disclosed technology.

FIG. 2 is a flow chart showing an example of the flow of processing for inducing the differentiation of pluripotent stem cells, which is carried out in the cell culture apparatus 100.

In step S1, cells are cultured in a culture medium to which a first additive containing a Wnt signaling activator has been added.

After a predetermined time has elapsed from the start of culture in the culture medium to which the first additive has been added, the culture medium is exchanged in step S2. In addition, the first culture medium exchange after the culture is started is referred to as culture medium exchange [1]. The period from the start of culture to the completion of culture medium exchange [1] is, for example, about 0.5 days to 2 days.

In step S3, the first additive containing a Wnt signaling activator is re-added to the culture medium.

After a predetermined time has elapsed following the re-addition of the first additive, the culture medium is exchanged in step S4. In addition, the culture medium exchange after the re-addition of the first additive is referred to as culture medium exchange [2].

In step S5, it is determined whether or not the number of processing cycles in which a series of processes including re-addition of the first additive and culture medium exchange [2] is one unit has reached a predetermined number of cycles. A series of processes including re-addition of the first additive and culture medium exchange [2] are repeatedly carried out until the number of process cycles reaches the predetermined number of cycles. One cycle period of a series of processes including re-addition of the first additive and culture medium exchange [2] is, for example, about 1 to 5 days.

In step S6, the cells are cultured in a culture medium to which the second additive containing a Wnt signaling inhibitor has been added.

After a predetermined time has elapsed following the addition of the second additive, the culture medium is exchanged in step S7. In addition, the first culture medium exchange after addition of the second additive is referred to as culture medium exchange [3]. The period from the addition of the second additive to the completion of culture medium exchange [2] is, for example, about 0.5 days to 2 days.

In step S8, the second additive containing a Wnt signaling inhibitor is re-added to the culture medium.

After a predetermined time has elapsed following the re-addition of the second additive, the culture medium is exchanged in step S9. In addition, the culture medium exchange after the re-addition of the second additive is referred to as culture medium exchange [4].

In step S10, it is determined whether or not the number of processing cycles in which a series of processes including re-addition of the second additive and culture medium exchange [4] is one unit has reached a predetermined number of cycles. A series of processes including re-addition of the second additive and culture medium exchange [4] are repeatedly carried out until the number of process cycles reaches the predetermined number of cycles. One cycle period of a series of processes including re-addition of the second additive and culture medium exchange [4] is, for example, about 1 to 5 days.

The operation of the cell culture apparatus 100 corresponding to each of the foregoing steps will be described below. From the viewpoint of avoiding the complexity of the description, the following description refers only to a case of controlling the on-off valves V1 to V14 in an open state with respect to the opening/closing control of the on-off valves V1 to V14. After the on-off valves V1 to V14 are controlled to be in an open state, the valves are appropriately controlled to be in a closed state.

<Addition of First Additive>

Figure 3:
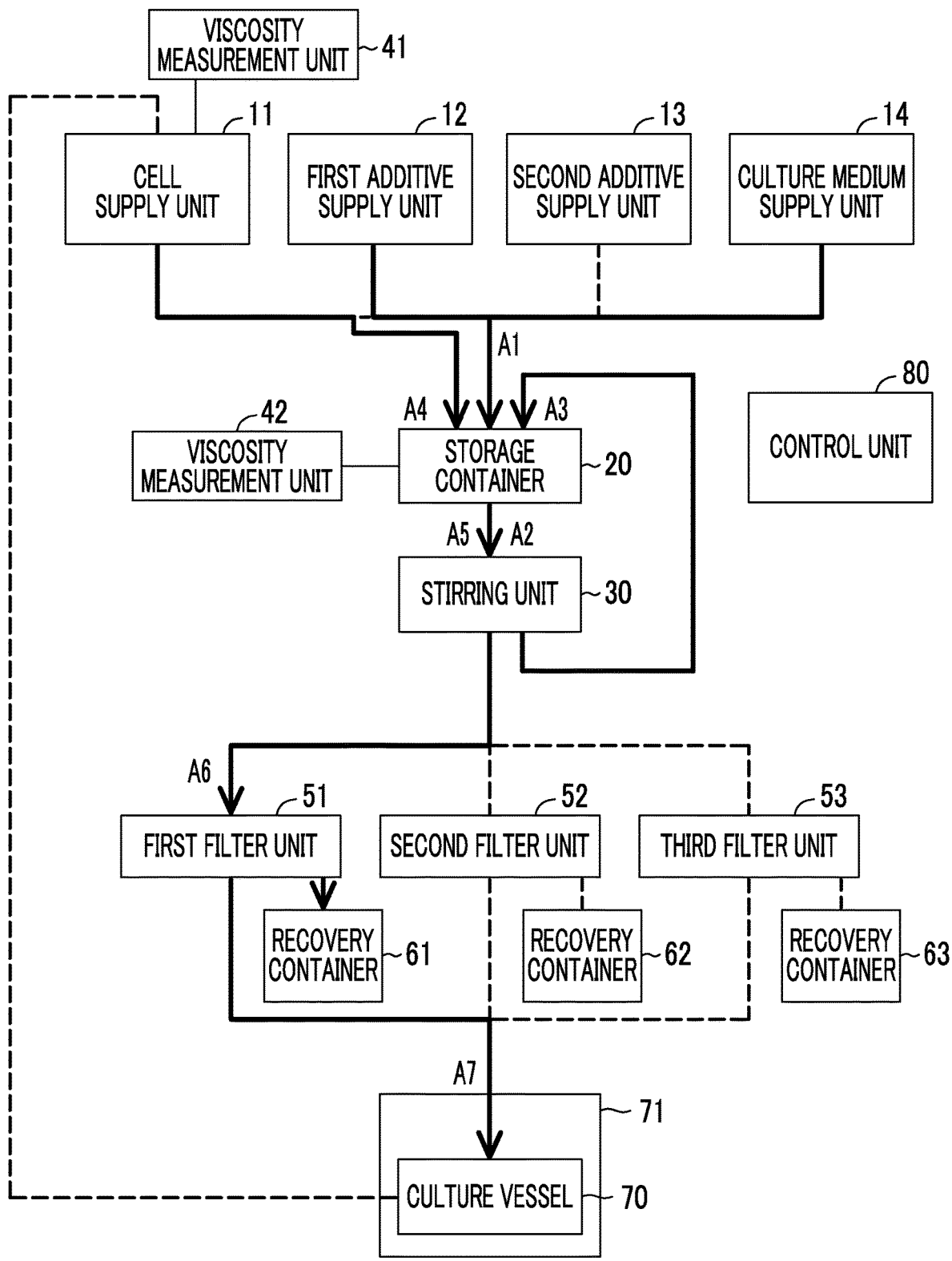
FIG. 3 is a diagram showing an operation of the cell culture apparatus in a case of carrying out a process of adding a first additive according to an embodiment of the disclosed technology.

FIG. 3 is a diagram showing an operation of the cell culture apparatus 100 in a case of carrying out the process carried out in step S1 shown in FIG. 2, that is, the process of adding the first additive. In FIG. 3, the order of supplying the processing targets (cell suspension, culture medium, additive, and a mixture thereof) to the respective processing units is shown. The cell supply unit 11 is assumed to accommodate a cell suspension containing pluripotent stem cells that are subjected to induction of differentiation using the cell culture apparatus 100. In addition, it is assumed that the viscosity of the cell suspension accommodated in the cell supply unit 11 is measured by the viscosity measurement unit 41, and the measurement results are notified to the control unit 80.

In step A1, the control unit 80 controls the on-off valves V2 and V4 in an open state and drives a predetermined pump. As a result, the first additive containing a Wnt signaling activator is supplied from the first additive supply unit 12 to the storage container 20, and a fresh culture medium is supplied from the culture medium supply unit 14 to the storage container 20. As a result, a mixture containing the first additive and the fresh culture medium is accommodated in the storage container 20. The viscosity of the mixture containing the first additive and the fresh culture medium accommodated in the storage container 20 is measured by the viscosity measurement unit 42, and the measurement results are notified to the control unit 80.

Here, it is assumed that the viscosity of the mixture containing the first additive and the fresh culture medium accommodated in the storage container 20 is higher than the viscosity of the cell suspension accommodated in the cell supply unit 11. The mixture containing the first additive and the fresh culture medium and the cell suspension will be mixed later, but in a case where the viscosity difference between the mixture containing the first additive and the fresh culture medium and the cell suspension is large, a satisfactory mixing state may not be obtained. Therefore, it is preferred that, after making the viscosity of the mixture containing the first additive and the fresh culture medium equal to the viscosity of the cell suspension, the mixture containing the first additive and the fresh culture medium and the cell suspension are mixed. The mixture containing the first additive and the fresh culture medium has a thixotropic property and it is possible to lower the viscosity of the mixture by adding a shear stress. Therefore, the control unit 80 carries out control of the feeding of liquid for applying a shear stress to the mixture containing the first additive and the fresh culture medium, and then combining the cell suspension and the above mixture and transferring the combined mixture to the stirring unit 30. Specifically, the control unit 80 circulates the mixture containing the first additive and the fresh culture medium between the storage container 20 and the stirring unit 30 to thereby apply a shear stress to the mixture.

That is, in step A2, the control unit 80 controls the on-off valves V5 and V6 in an open state and drives a predetermined pump. As a result, the mixture containing the first additive and the fresh culture medium accommodated in the storage container 20 is transferred to the stirring unit 30 through the flow channel F2. The mixture containing the first additive and the fresh culture medium is stirred in the stirring unit 30 so that a shear stress is applied to the mixture, thus resulting in a reduced viscosity thereof.

Subsequently, in step A3, the control unit 80 controls the on-off valves V13 and V14 in an open state and drives a predetermined pump. As a result, the mixture containing the first additive and the fresh culture medium which has passed through the stirring unit 30 is returned to the storage container 20 through the flow channel F20. The viscosity of the mixture containing the first additive and the fresh culture medium accommodated in the storage container 20 is measured by the viscosity measurement unit 42, and the measurement results are notified to the control unit 80. The control unit 80 continuously carries out the feeding of liquid which circulates the mixture between the storage container 20 and the stirring unit 30 until the difference value between the viscosity of the mixture notified from the viscosity measurement unit 42 and the viscosity of the cell suspension notified from the viscosity measurement unit 41 becomes equal to or less than a predetermined value. Further, the control unit 80 may continuously carry out the feeding of liquid which circulates the mixture between the storage container 20 and the stirring unit 30 until the viscosity value of the mixture notified from the viscosity measurement unit 42 becomes less than or equal to the predetermined value regardless of the viscosity of the cell suspension notified from the viscosity measurement unit 41. Further, the control unit 80 may continuously carry out the feeding of liquid which circulates the mixture between the storage container 20 and the stirring unit 30 until the number of processing cycles reaches a predetermined number of cycles.

In a case where the feeding of liquid for applying a shear stress to the mixture containing the first additive and the fresh culture medium is completed, in step A4, the control unit 80 controls the on-off valve V1 in an open state and drives a predetermined pump. As a result, the cell suspension accommodated in the cell supply unit 11 is transferred to the storage container 20 through the flow channel F1 and is then combined with the mixture containing the first additive and the fresh culture medium whose viscosity has been adjusted.

In step A5, the control unit 80 controls the on-off valves V5 and V6 in an open state and drives a predetermined pump. As a result, a mixture containing the cell suspension, the first additive, and the fresh culture medium is transferred from the storage container 20 to the stirring unit 30 through the flow channel F2. The mixture containing the cell suspension, the first additive, and the fresh culture medium is stirred and mixed in the stirring unit 30. By applying a shear stress to the mixture containing the first additive and the fresh culture medium to carry out viscosity adjustment, a satisfactory mixing state can be obtained in the mixture containing the cell suspension, the first additive, and the fresh culture medium.

In step A6, the control unit 80 controls the on-off valves V7 and V8 in an open state and drives a predetermined pump. As a result, the mixture containing the cell suspension, the first additive, and the fresh culture medium is supplied from the stirring unit 30 to the first filter unit 51 of the separation unit 50 through the flow channel F3. The mixture containing the cell suspension, the first additive, and the fresh culture medium is subjected to a membrane separation process in the first filter unit 51 to separate living cells from dead cells. The filtrate containing the dead cells that have permeated the filter membrane of the first filter unit 51 is recovered in the recovery container 61.

In step A7, the control unit 80 controls an on-off valve V11 in an open state and drives a predetermined pump. As a result, a mixture containing the cell suspension from which dead cells have been removed, the first additive, and the fresh culture medium is supplied from the first filter unit 51 to the culture vessel 70 through the flow channel F4. The pluripotent stem cells are accommodated in the culture vessel 70 together with the culture medium to which the first additive containing a Wnt signaling activator has been added, whereby the culture for the induction of differentiation is started.

<Culture Medium Exchange [1]>

Figure 4:
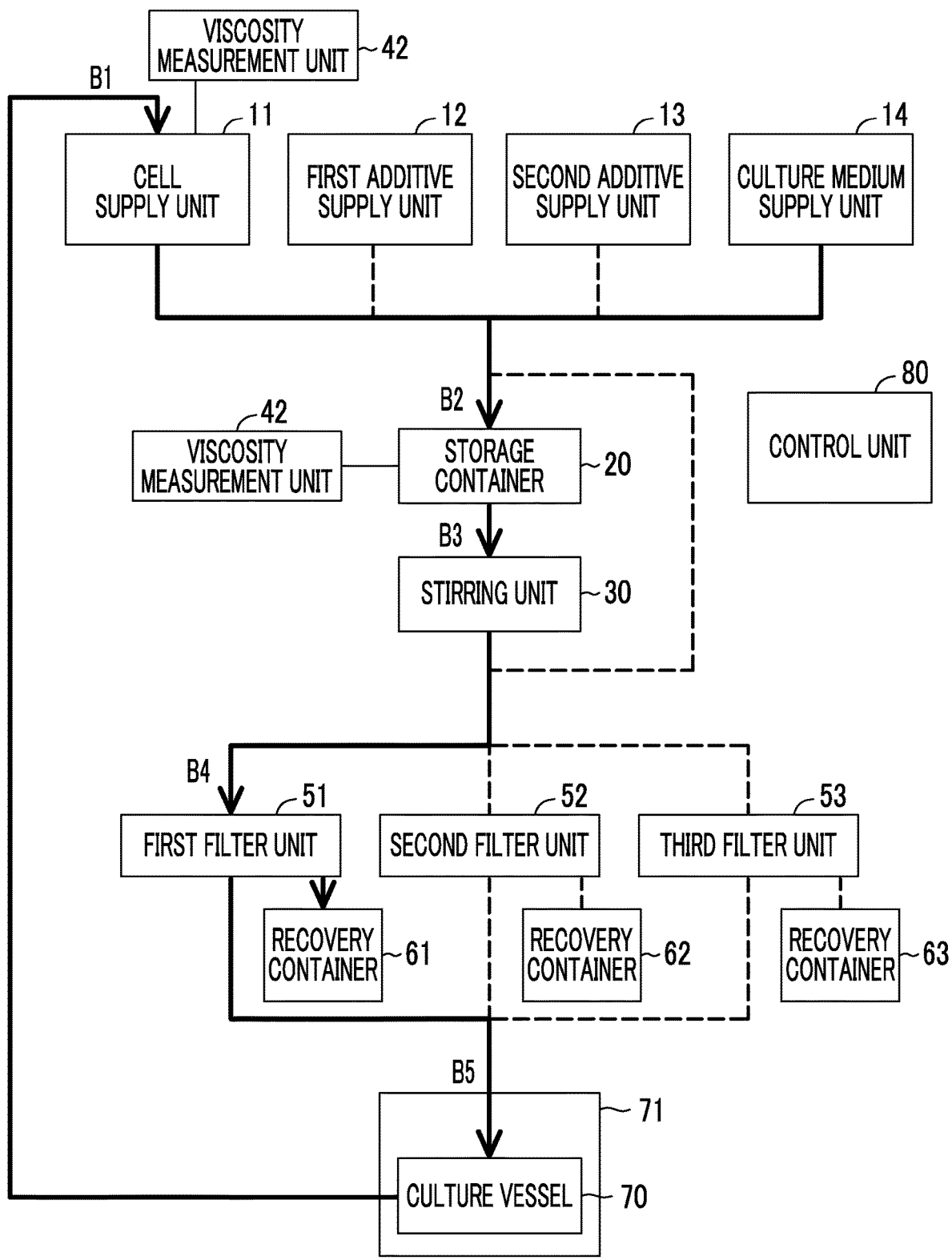
FIG. 4 is a diagram showing the operation of the cell culture apparatus in a case of carrying out a culture medium exchange process according to an embodiment of the disclosed technology.

FIG. 4 is a diagram showing an operation of the cell culture apparatus 100 in a case of carrying out the process carried out in step S2 shown in FIG. 2, that is, culture medium exchange [1]. In FIG. 4, the order of supplying the processing targets (cell suspension, culture medium, additive, and a mixture thereof) to the respective processing units is shown.

In step B1, the control unit 80 controls an on-off valve V12 in an open state and drives a predetermined pump. As a result, the cell suspension containing the spent culture medium is transferred from the culture vessel 70 to the cell supply unit 11 through the flow channel F5.

In step B2, the control unit 80 controls the on-off valves V1 and V4 in an open state and drives a predetermined pump. As a result, the cell suspension containing the spent culture medium is transferred from the cell supply unit 11 to the storage container 20 through the flow channel F1, and a fresh culture medium is supplied from the culture medium supply unit 14 to the storage container 20.

In step B3, the control unit 80 controls the on-off valves V5 and V6 in an open state and drives a predetermined pump. As a result, the cell suspension to which the fresh culture medium has been added is transferred from the storage container 20 to the stirring unit 30 through the flow channel F2. The cell suspension to which the fresh culture medium has been added is stirred and mixed in the stirring unit 30.

In step B4, the control unit 80 controls the on-off valves V7 and V8 in an open state and drives a predetermined pump. As a result, the cell suspension to which the fresh culture medium has been added is supplied from the stirring unit 30 to the first filter unit 51 of the separation unit 50 through the flow channel F3. The cell suspension to which the fresh culture medium has been added is subjected to a membrane separation process in the first filter unit 51, and a part of the mixture containing the spent culture medium and the fresh culture medium is removed together with the dead cells. The filtrate containing the dead cells that have permeated the filter membrane of the first filter unit 51 is recovered in the recovery container 61.

In step B5, the control unit 80 controls the on-off valve V11 in an open state and drives a predetermined pump. As a result, the cell suspension subjected to the membrane separation process is supplied from the first filter unit 51 to the culture vessel 70 through the flow channel F4, and therefore the culture medium exchange process is completed.

<Re-Addition of First Additive>

Figure 5:
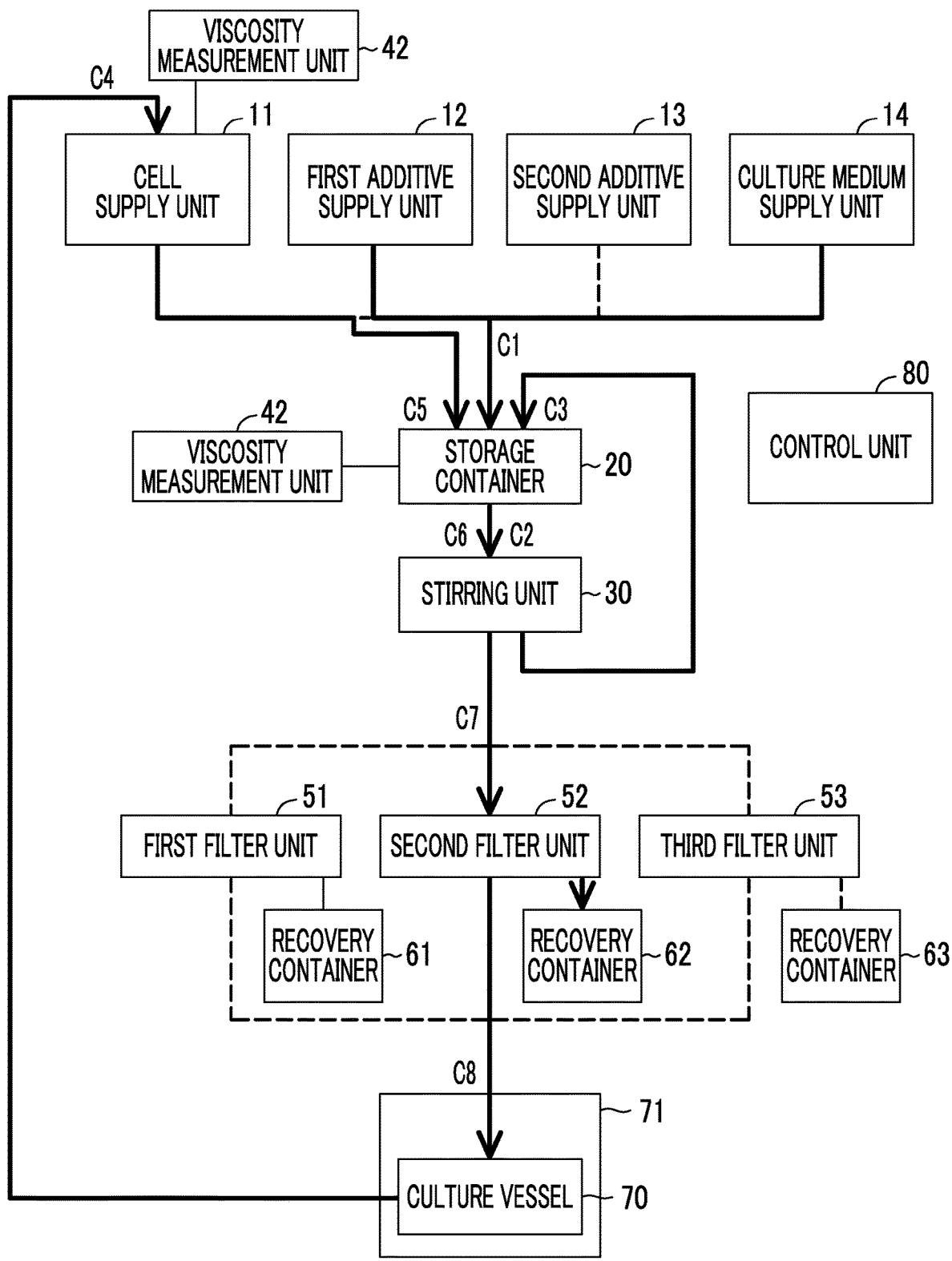
FIG. 5 is a diagram showing the operation of the cell culture apparatus in a case of re-adding the first additive according to an embodiment of the disclosed technology.

FIG. 5 is a diagram showing an operation of the cell culture apparatus 100 in a case of carrying out the process carried out in step S3 shown in FIG. 2, that is, the process of re-adding the first additive. In FIG. 5, the order of supplying the processing targets (cell suspension, culture medium, additive, and a mixture thereof) to the respective processing units is shown.

In step C1, the control unit 80 controls the on-off valves V2 and V4 in an open state and drives a predetermined pump. As a result, the first additive containing a Wnt signaling activator is supplied from the first additive supply unit 12 to the storage container 20, and a fresh culture medium is supplied from the culture medium supply unit 14 to the storage container 20. As a result, a mixture containing the first additive and the fresh culture medium is accommodated in the storage container 20. The viscosity of the mixture containing the first additive and the fresh culture medium accommodated in the storage container 20 is measured by the viscosity measurement unit 42, and the measurement results are notified to the control unit 80.

Here, it is assumed that the viscosity of the mixture containing the first additive and the fresh culture medium accommodated in the storage container 20 is higher than the viscosity of the cell suspension accommodated in the culture vessel 70. The mixture containing the first additive and the fresh culture medium and the cell suspension will be mixed later, but in a case where the viscosity difference between the mixture containing the first additive and the fresh culture medium and the cell suspension is large, a satisfactory mixing state may not be obtained. Therefore, it is preferred that, after making the viscosity of the mixture containing the first additive and the fresh culture medium equal to the viscosity of the cell suspension, the mixture containing the first additive and the fresh culture medium and the cell suspension are mixed. The mixture containing the first additive and the fresh culture medium has a thixotropic property and it is possible to lower the viscosity of the mixture by adding a shear stress. Therefore, the control unit 80 carries out control of the feeding of liquid for applying a shear stress to the mixture containing the first additive and the fresh culture medium, and then combining the cell suspension and the above mixture and transferring the combined mixture to the stirring unit 30. Specifically, the control unit 80 circulates the mixture containing the first additive and the fresh culture medium between the storage container 20 and the stirring unit 30 to thereby apply a shear stress to the mixture.

That is, in step C2, the control unit 80 controls the on-off valves V5 and V6 in an open state and drives a predetermined pump. As a result, the mixture containing the first additive and the fresh culture medium accommodated in the storage container 20 is transferred to the stirring unit 30 through the flow channel F2. The mixture containing the first additive and the fresh culture medium is stirred in the stirring unit 30 so that a shear stress is applied to the mixture, thus resulting in a reduced viscosity thereof.

Subsequently, in step C3, the control unit 80 controls the on-off valves V13 and V14 in an open state and drives a predetermined pump. As a result, the mixture containing the first additive and the fresh culture medium which has passed through the stirring unit 30 is returned to the storage container 20 through the flow channel F20. The viscosity of the mixture containing the first additive and the fresh culture medium accommodated in the storage container 20 is measured by the viscosity measurement unit 42, and the measurement results are notified to the control unit 80. The control unit 80 continuously carries out the feeding of liquid which circulates the mixture between the storage container 20 and the stirring unit 30 until the value of the viscosity of the mixture notified from the viscosity measurement unit 42 becomes equal to or less than a predetermined value. Further, the control unit 80 may continuously carry out the feeding of liquid which circulates the mixture between the storage container 20 and the stirring unit 30 until the number of processing cycles reaches a predetermined number of cycles.

In a case where the feeding of liquid for applying a shear stress to the mixture containing the first additive and the fresh culture medium is completed, in step C4, the control unit 80 controls the on-off valve V12 in an open state and drives a predetermined pump. As a result, the cell suspension is transferred from the culture vessel 70 to the cell supply unit 11 through the flow channel F5.

In step C5, the control unit 80 controls the on-off valve V1 in an open state and drives a predetermined pump. As a result, the cell suspension accommodated in the cell supply unit 11 is transferred to the storage container 20 through the flow channel F1 and is then combined with the mixture containing the first additive and the fresh culture medium whose viscosity has been adjusted.

In step C6, the control unit 80 controls the on-off valves V5 and V6 in an open state and drives a predetermined pump. As a result, a mixture containing the cell suspension, the first additive, and the fresh culture medium is transferred from the storage container 20 to the stirring unit 30 through the flow channel F2. The mixture containing the cell suspension, the first additive, and the fresh culture medium is stirred and mixed in the stirring unit 30. By applying a shear stress to the mixture containing the first additive and the fresh culture medium to carry out viscosity adjustment, a satisfactory mixing state can be obtained in the mixture containing the cell suspension, the first additive, and the fresh culture medium.

In step C7, the control unit 80 controls the on-off valves V7 and V9 in an open state and drives a predetermined pump. As a result, a mixture containing the cell suspension, the first additive, and the fresh culture medium is supplied from the stirring unit 30 to the second filter unit 52 of the separation unit 50 through the flow channel F3. The mixture containing the cell suspension, the first additive, and the fresh culture medium is subjected to a membrane separation process in the second filter unit 52 to separate undifferentiated cells that do not differentiate into intermediates (ectoderm, mesoderm, and endoderm) and dead cells from the intermediates. The filtrate containing the undifferentiated cells and the dead cells that have permeated the filter membrane of the second filter unit 52 is recovered in the recovery container 62.

In step C8, the control unit 80 controls the on-off valve V11 in an open state and drives a predetermined pump. As a result, undifferentiated cells and dead cells are removed, and a mixture containing the cell suspension in which the intermediates are left, the first additive, and the fresh culture medium is supplied from the second filter unit 52 to the culture vessel 70 through the flow channel F4.

<Culture Medium Exchange [2]>

Figure 6:
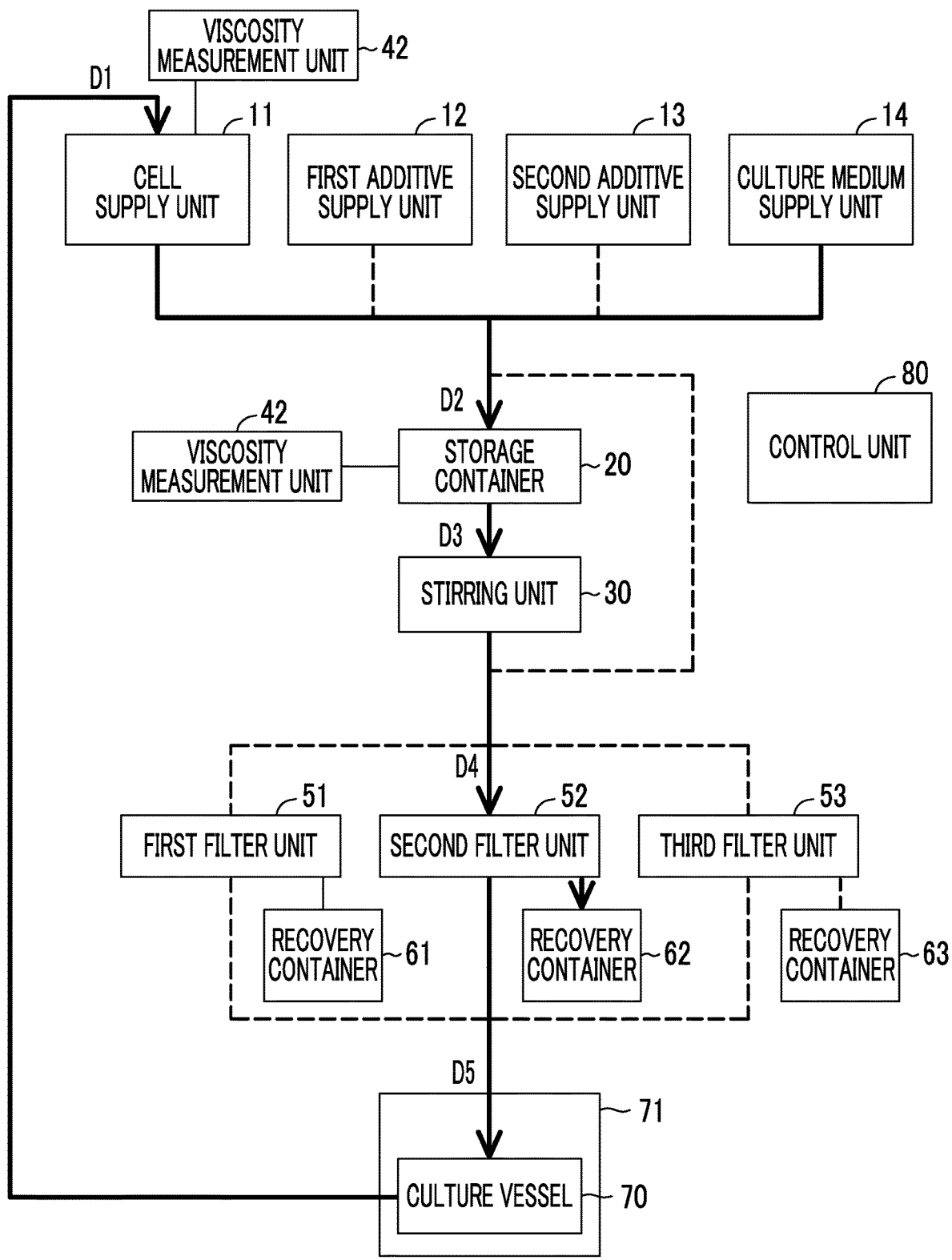
FIG. 6 is a diagram showing the operation of the cell culture apparatus in a case of carrying out the culture medium exchange process according to an embodiment of the disclosed technology.

FIG. 6 is a diagram showing an operation of the cell culture apparatus 100 in a case of carrying out the process carried out in step S4 shown in FIG. 2, that is, culture medium exchange [2]. In FIG. 6, the order of supplying the processing targets (cell suspension, culture medium, additive, and a mixture thereof) to the respective processing units is shown.

In step D1, the control unit 80 controls the on-off valve V12 in an open state and drives a predetermined pump. As a result, the cell suspension containing the spent culture medium is transferred from the culture vessel 70 to the cell supply unit 11 through the flow channel F5.

In step D2, the control unit 80 controls the on-off valves V1 and V4 in an open state and drives a predetermined pump. As a result, the cell suspension containing the spent culture medium is transferred from the cell supply unit 11 to the storage container 20 through the flow channel F1, and a fresh culture medium is supplied from the culture medium supply unit 14 to the storage container 20.

In step D3, the control unit 80 controls the on-off valves V5 and V6 in an open state and drives a predetermined pump. As a result, the cell suspension to which the fresh culture medium has been added is transferred from the storage container 20 to the stirring unit 30 through the flow channel F2. The cell suspension to which the fresh culture medium has been added is stirred and mixed in the stirring unit 30.

In step D4, the control unit 80 controls the on-off valves V7 and V9 in an open state and drives a predetermined pump. As a result, the cell suspension to which the fresh culture medium has been added is supplied from the stirring unit 30 to the second filter unit 52 of the separation unit 50 through the flow channel F3. The cell suspension to which the fresh culture medium has been added is subjected to a membrane separation process in the second filter unit 52, and a part of the mixture containing the spent culture medium and the fresh culture medium is removed together with the dead cells and the undifferentiated cells. The filtrate containing the dead cells and the undifferentiated cells that have permeated the filter membrane of the second filter unit 52 is recovered in the recovery container 62.

In step D5, the control unit 80 controls the on-off valve V11 in an open state and drives a predetermined pump. As a result, the cell suspension subjected to the membrane separation process is supplied from the second filter unit 52 to the culture vessel 70 through the flow channel F4, and therefore the culture medium exchange process is completed.

<Addition of Second Additive>

Figure 7:
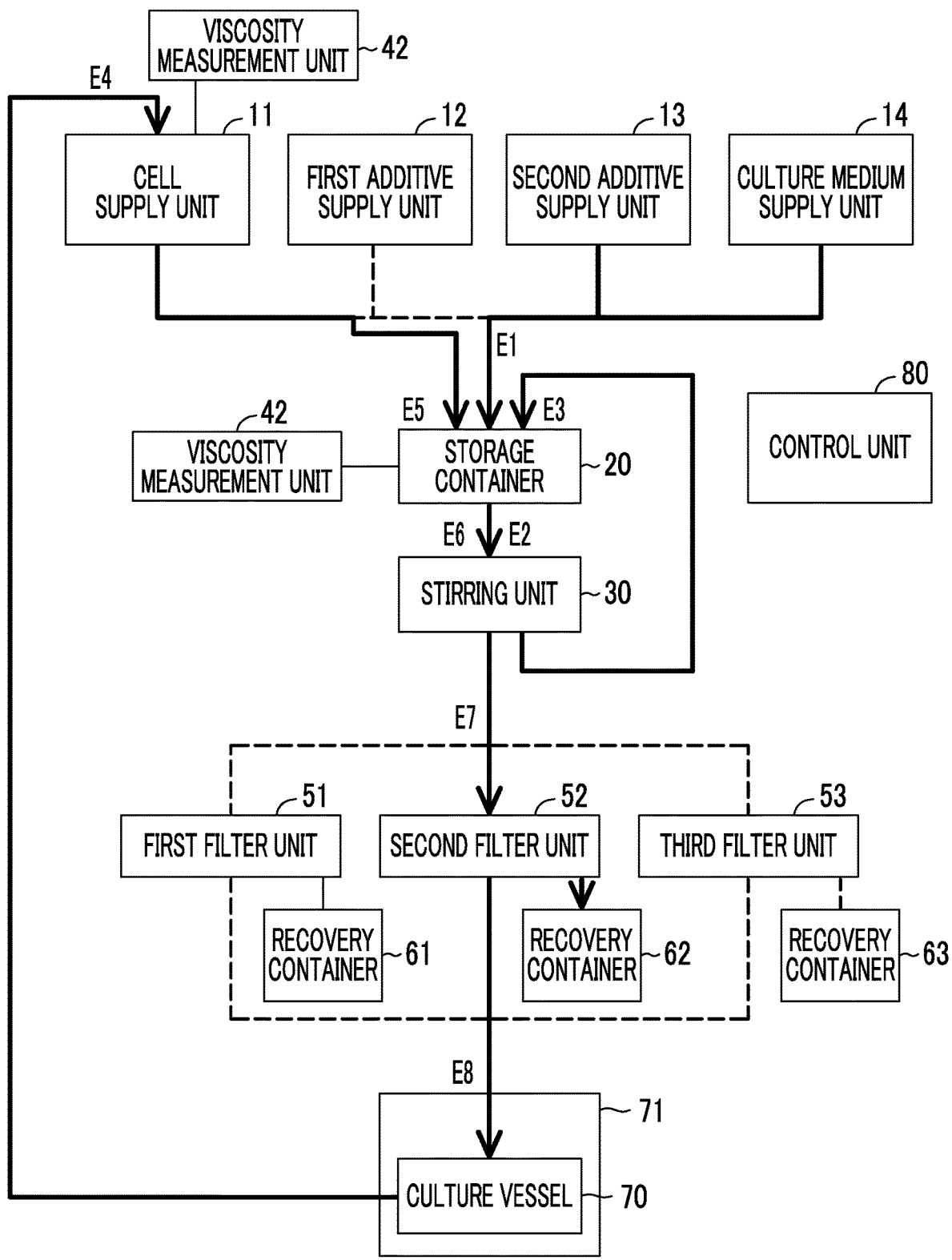
FIG. 7 is a diagram showing the operation of the cell culture apparatus in a case of adding a second additive according to an embodiment of the disclosed technology.

FIG. 7 is a diagram showing an operation of the cell culture apparatus 100 in a case of carrying out the process carried out in step S6 shown in FIG. 2, that is, the process of adding a second additive. In FIG. 7, the order of supplying the processing targets (cell suspension, culture medium, additive, and a mixture thereof) to the respective processing units is shown.

In step E1, the control unit 80 controls the on-off valves V3 and V4 in an open state and drives a predetermined pump. As a result, the second additive containing a Wnt signaling inhibitor is supplied from the second additive supply unit 13 to the storage container 20, and a fresh culture medium is supplied from the culture medium supply unit 14 to the storage container 20. As a result, a mixture containing the second additive and the fresh culture medium is accommodated in the storage container 20. The viscosity of the mixture containing the second additive and the fresh culture medium accommodated in the storage container 20 is measured by the viscosity measurement unit 42, and the measurement results are notified to the control unit 80.

Here, it is assumed that the viscosity of the mixture containing the second additive and the fresh culture medium accommodated in the storage container 20 is higher than the viscosity of the cell suspension accommodated in the culture vessel 70. The mixture containing the second additive and the fresh culture medium and the cell suspension will be mixed later, but in a case where the viscosity difference between the mixture containing the second additive and the fresh culture medium and the cell suspension is large, a satisfactory mixing state may not be obtained. Therefore, it is preferred that, after making the viscosity of the mixture containing the second additive and the fresh culture medium equal to the viscosity of the cell suspension, the mixture containing the second additive and the fresh culture medium and the cell suspension are mixed. The mixture containing the second additive and the fresh culture medium has a thixotropic property and it is possible to lower the viscosity of the mixture by adding a shear stress. Therefore, the control unit 80 carries out control of the feeding of liquid for applying a shear stress to the mixture containing the second additive and the fresh culture medium, and then combining the cell suspension and the above mixture and transferring the combined mixture to the stirring unit 30. Specifically, the control unit 80 circulates the mixture containing the second additive and the fresh culture medium between the storage container 20 and the stirring unit 30 to thereby apply a shear stress to the mixture.

That is, in step E2, the control unit 80 controls the on-off valves V5 and V6 in an open state and drives a predetermined pump. As a result, the mixture containing the second additive and the fresh culture medium accommodated in the storage container 20 is transferred to the stirring unit 30 through the flow channel F2. The mixture containing the second additive and the fresh culture medium is stirred in the stirring unit 30 so that a shear stress is applied to the mixture, thus resulting in a reduced viscosity thereof.

Subsequently, in step E3, the control unit 80 controls the on-off valves V13 and V14 in an open state and drives a predetermined pump. As a result, the mixture containing the second additive and the fresh culture medium which has passed through the stirring unit 30 is returned to the storage container 20 through the flow channel F20. The viscosity of the mixture containing the second additive and the fresh culture medium accommodated in the storage container 20 is measured by the viscosity measurement unit 42, and the measurement results are notified to the control unit 80. The control unit 80 continuously carries out the feeding of liquid which circulates the mixture between the storage container 20 and the stirring unit 30 until the value of the viscosity of the mixture notified from the viscosity measurement unit 42 becomes equal to or less than a predetermined value. Further, the control unit 80 may continuously carry out the feeding of liquid which circulates the mixture between the storage container 20 and the stirring unit 30 until the number of processing cycles reaches a predetermined number of cycles.

In a case where the feeding of liquid for applying a shear stress to the mixture containing the second additive and the fresh culture medium is completed, in step E4, the control unit 80 controls the on-off valve V12 in an open state and drives a predetermined pump. As a result, the cell suspension is transferred from the culture vessel 70 to the cell supply unit 11 through the flow channel F5.

In step E5, the control unit 80 controls the on-off valve V1 in an open state and drives a predetermined pump. As a result, the cell suspension accommodated in the cell supply unit 11 is transferred to the storage container 20 through the flow channel F1 and is then combined with the mixture containing the second additive and the fresh culture medium whose viscosity has been adjusted.

In step E6, the control unit 80 controls the on-off valves V5 and V6 in an open state and drives a predetermined pump. As a result, a mixture containing the cell suspension, the second additive, and the fresh culture medium is transferred from the storage container 20 to the stirring unit 30 through the flow channel F2. The mixture containing the cell suspension, the second additive, and the fresh culture medium is stirred and mixed in the stirring unit 30. By applying a shear stress to the mixture containing the second additive and the fresh culture medium to carry out viscosity adjustment, a satisfactory mixing state can be obtained in the mixture containing the cell suspension, the second additive, and the fresh culture medium.

In step E7, the control unit 80 controls the on-off valves V7 and V9 in an open state and drives a predetermined pump. As a result, a mixture containing the cell suspension, the second additive, and the fresh culture medium is supplied from the stirring unit 30 to the second filter unit 52 of the separation unit 50 through the flow channel F3. The mixture containing the cell suspension, the second additive, and the fresh culture medium is subjected to a membrane separation process in the second filter unit 52 to separate undifferentiated cells that do not differentiate into intermediates (ectoderm, mesoderm, and endoderm) and dead cells from the intermediates. The filtrate containing the undifferentiated cells and the dead cells that have permeated the filter membrane of the second filter unit 52 is recovered in the recovery container 62.

In step E8, the control unit 80 controls the on-off valve V11 in an open state and drives a predetermined pump. As a result, undifferentiated cells and dead cells are removed, and a mixture containing the cell suspension in which the intermediates are left, the second additive, and the fresh culture medium is supplied from the second filter unit 52 to the culture vessel 70 through the flow channel F4.

<Culture Medium Exchange [3]>

Figure 8:
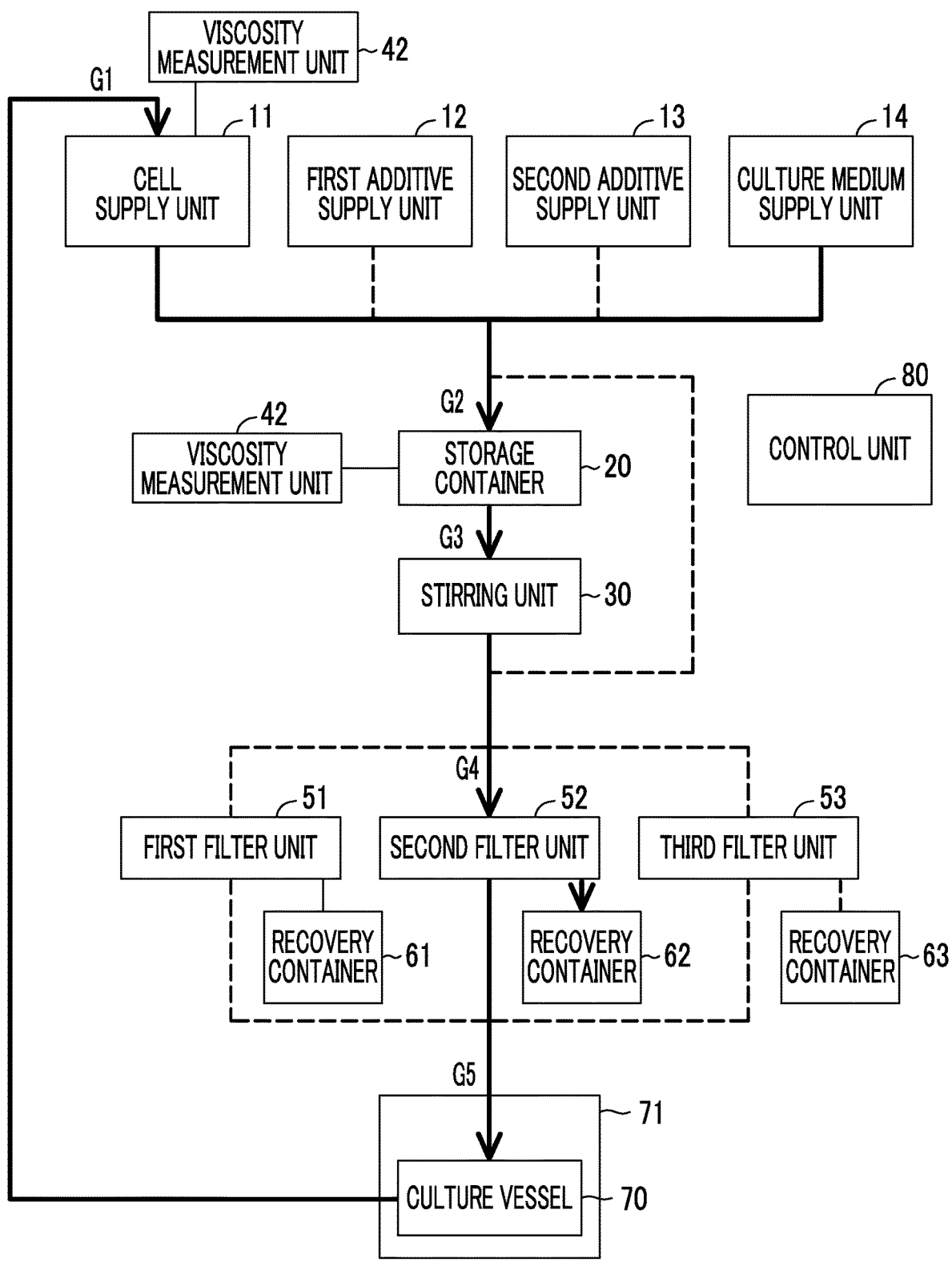
FIG. 8 is a diagram showing the operation of the cell culture apparatus in a case of carrying out the culture medium exchange process according to the embodiment of the disclosed technology.

FIG. 8 is a diagram showing an operation of the cell culture apparatus 100 in a case of carrying out the process carried out in step S7 shown in FIG. 2, that is, culture medium exchange [3]. In FIG. 8, the order of supplying the processing targets (cell suspension, culture medium, additive, and a mixture thereof) to the respective processing units is shown.

In step G1, the control unit 80 controls the on-off valve V12 in an open state and drives a predetermined pump. As a result, the cell suspension containing the spent culture medium is transferred from the culture vessel 70 to the cell supply unit 11 through the flow channel F5.

In step G2, the control unit 80 controls the on-off valves V1 and V4 in an open state and drives a predetermined pump. As a result, the cell suspension containing the spent culture medium is transferred from the cell supply unit 11 to the storage container 20 through the flow channel F1, and a fresh culture medium is supplied from the culture medium supply unit 14 to the storage container 20.

In step G3, the control unit 80 controls the on-off valves V5 and V6 in an open state and drives a predetermined pump. As a result, the cell suspension to which the fresh culture medium has been added is transferred from the storage container 20 to the stirring unit 30 through the flow channel F2. The cell suspension to which the fresh culture medium has been added is stirred and mixed in the stirring unit 30.

In step G4, the control unit 80 controls the on-off valves V7 and V9 in an open state and drives a predetermined pump. As a result, the cell suspension to which the fresh culture medium has been added is supplied from the stirring unit 30 to the second filter unit 52 of the separation unit 50 through the flow channel F3. The cell suspension to which the fresh culture medium has been added is subjected to a membrane separation process in the second filter unit 52, and a part of the mixture containing the spent culture medium and the fresh culture medium is removed together with the dead cells and the undifferentiated cells. The filtrate containing the dead cells and the undifferentiated cells that have permeated the filter membrane of the second filter unit 52 is recovered in the recovery container 62.

In step G5, the control unit 80 controls the on-off valve V11 in an open state and drives a predetermined pump. As a result, the cell suspension subjected to the membrane separation process is supplied from the second filter unit 52 to the culture vessel 70 through the flow channel F4, and therefore the culture medium exchange process is completed.

<Re-Addition of Second Additive>

Figure 9:
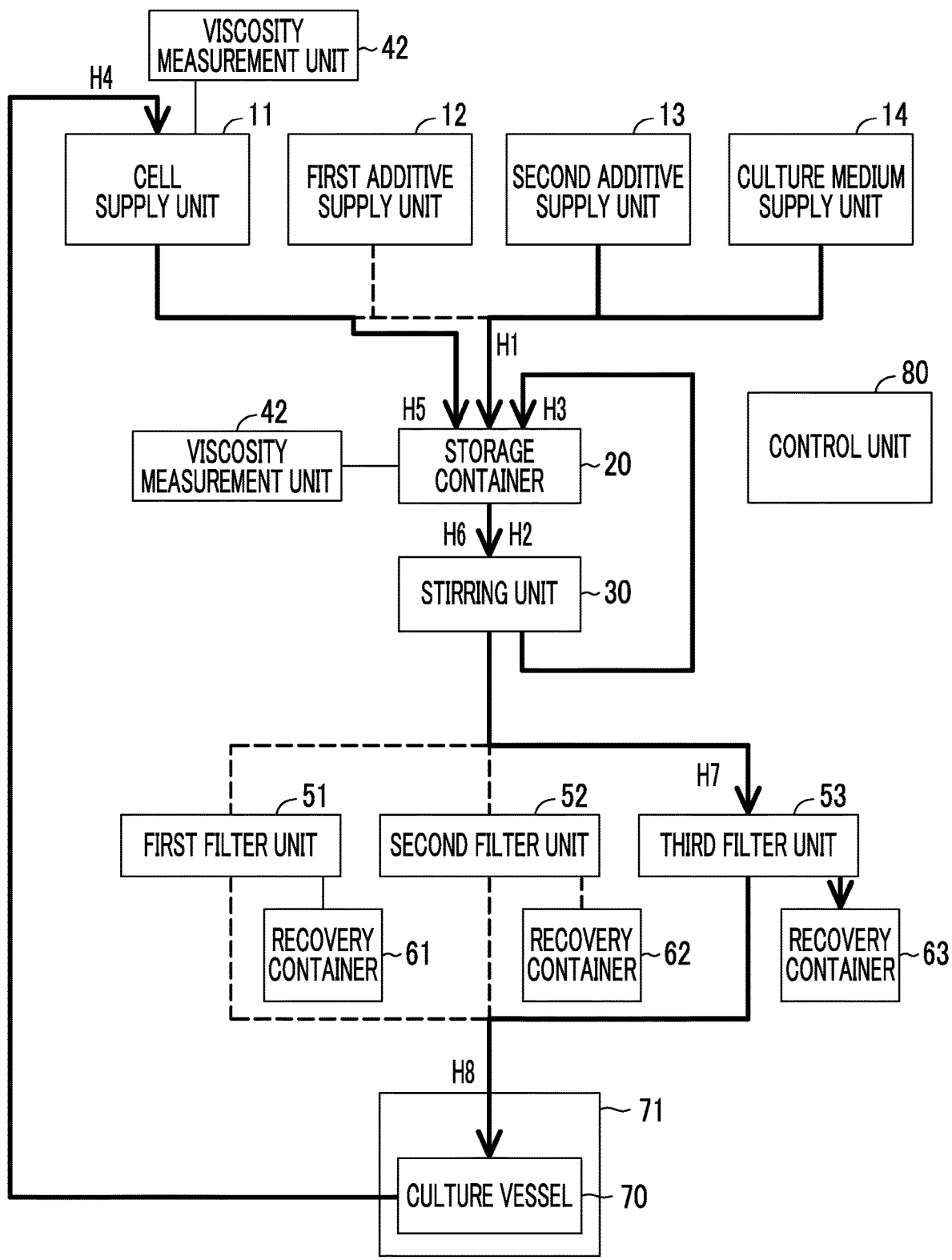
FIG. 9 is a diagram showing the operation of the cell culture apparatus in a case of re-adding the second additive according to the embodiment of the disclosed technology.

FIG. 9 is a diagram showing an operation of the cell culture apparatus 100 in a case of carrying out the process carried out in step S8 shown in FIG. 2, that is, the process of re-adding the second additive. In FIG. 9, the order of supplying the processing targets (cell suspension, culture medium, additive, and a mixture thereof) to the respective processing units is shown.

In step H1, the control unit 80 controls the on-off valves V3 and V4 in an open state and drives a predetermined pump. As a result, the second additive containing a Wnt signaling inhibitor is supplied from the second additive supply unit 13 to the storage container 20, and a fresh culture medium is supplied from the culture medium supply unit 14 to the storage container 20. As a result, a mixture containing the second additive and the fresh culture medium is accommodated in the storage container 20. The viscosity of the mixture containing the second additive and the fresh culture medium accommodated in the storage container 20 is measured by the viscosity measurement unit 42, and the measurement results are notified to the control unit 80.

Here, it is assumed that the viscosity of the mixture containing the second additive and the fresh culture medium accommodated in the storage container 20 is higher than the viscosity of the cell suspension accommodated in the culture vessel 70. The mixture containing the second additive and the fresh culture medium and the cell suspension will be mixed later, but in a case where the viscosity difference between the mixture containing the second additive and the fresh culture medium and the cell suspension is large, a satisfactory mixing state may not be obtained. Therefore, it is preferred that, after making the viscosity of the mixture containing the second additive and the fresh culture medium equal to the viscosity of the cell suspension, the mixture containing the second additive and the fresh culture medium and the cell suspension are mixed. The mixture containing the second additive and the fresh culture medium has a thixotropic property and it is possible to lower the viscosity of the mixture by adding a shear stress. Therefore, the control unit 80 carries out control of the feeding of liquid for applying a shear stress to the mixture containing the second additive and the fresh culture medium, and then combining the cell suspension and the above mixture and transferring the combined mixture to the stirring unit 30. Specifically, the control unit 80 circulates the mixture containing the second additive and the fresh culture medium between the storage container 20 and the stirring unit 30 to thereby apply a shear stress to the mixture.

That is, in step H2, the control unit 80 controls the on-off valves V5 and V6 in an open state and drives a predetermined pump. As a result, the mixture containing the second additive and the fresh culture medium accommodated in the storage container 20 is transferred to the stirring unit 30 through the flow channel F2. The mixture containing the second additive and the fresh culture medium is stirred in the stirring unit 30 so that a shear stress is applied to the mixture, thus resulting in a reduced viscosity thereof.

Subsequently, in step H3, the control unit 80 controls the on-off valves V13 and V14 in an open state and drives a predetermined pump. As a result, the mixture containing the second additive and the fresh culture medium which has passed through the stirring unit 30 is returned to the storage container 20 through the flow channel F20. The viscosity of the mixture containing the second additive and the fresh culture medium accommodated in the storage container 20 is measured by the viscosity measurement unit 42, and the measurement results are notified to the control unit 80. The control unit 80 continuously carries out the feeding of liquid which circulates the mixture between the storage container 20 and the stirring unit 30 until the value of the viscosity of the mixture notified from the viscosity measurement unit 42 becomes equal to or less than a predetermined value. Further, the control unit 80 may continuously carry out the feeding of liquid which circulates the mixture between the storage container 20 and the stirring unit 30 until the number of processing cycles reaches a predetermined number of cycles.

In a case where the feeding of liquid for applying a shear stress to the mixture containing the second additive and the fresh culture medium is completed, in step H4, the control unit 80 controls the on-off valve V12 in an open state and drives a predetermined pump. As a result, the cell suspension is transferred from the culture vessel 70 to the cell supply unit 11 through the flow channel F5.

In step H5, the control unit 80 controls the on-off valve V1 in an open state and drives a predetermined pump. As a result, the cell suspension accommodated in the cell supply unit 11 is transferred to the storage container 20 through the flow channel F1 and is then combined with the mixture containing the second additive and the fresh culture medium whose viscosity has been adjusted.

In step H6, the control unit 80 controls the on-off valves V5 and V6 in an open state and drives a predetermined pump. As a result, a mixture containing the cell suspension, the second additive, and the fresh culture medium is transferred from the storage container 20 to the stirring unit 30 through the flow channel F2. The mixture containing the cell suspension, the second additive, and the fresh culture medium is stirred and mixed in the stirring unit 30. By applying a shear stress to the mixture containing the second additive and the fresh culture medium to carry out viscosity adjustment, a satisfactory mixing state can be obtained in the mixture containing the cell suspension, the second additive, and the fresh culture medium.

In step H7, the control unit 80 controls the on-off valves V7 and V10 in an open state and drives a predetermined pump. As a result, a mixture containing the cell suspension, the second additive, and the fresh culture medium is supplied from the stirring unit 30 to the third filter unit 53 of the separation unit 50 through the flow channel F3. The mixture containing the cell suspension, the second additive, and the fresh culture medium is subjected to a membrane separation process in the third filter unit 53 to separate intermediates (ectoderm, mesoderm, and endoderm) which do not undergo a transition into differentiated cells, undifferentiated cells which do not differentiate into intermediates, and dead cells from the differentiated cells. The filtrate containing the intermediates, the undifferentiated cells, and the dead cells that have permeated the filter membrane of the third filter unit 53 is recovered in the recovery container 63.

In step H8, the control unit 80 controls the on-off valve V11 in an open state and drives a predetermined pump. As a result, intermediates, undifferentiated cells, and dead cells are removed, and a mixture containing the cell suspension in which the differentiated cells are left, the second additive, and the fresh culture medium is supplied from the third filter unit 53 to the culture vessel 70 through the flow channel F4.

<Culture Medium Exchange [4]>

Figure 10:
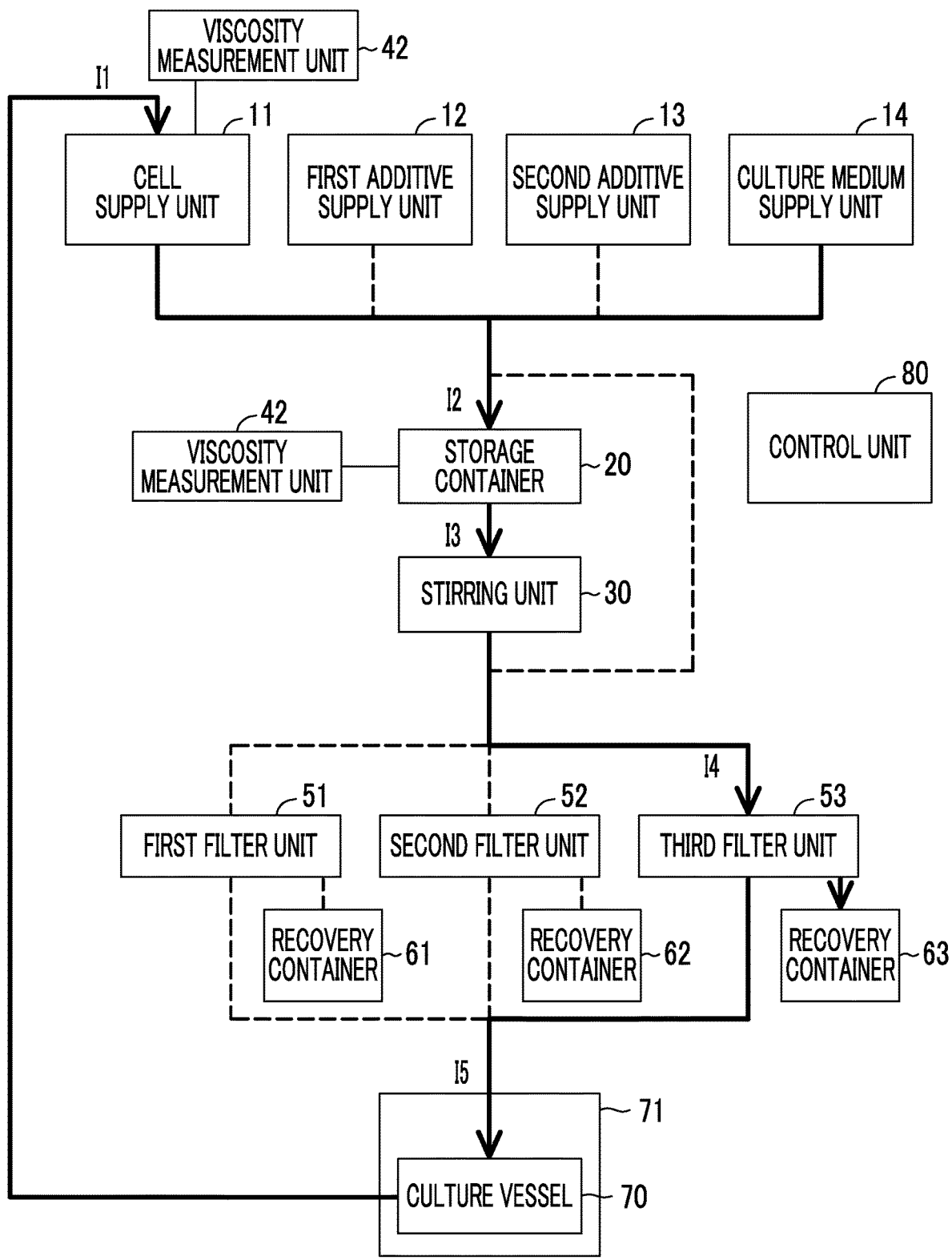
FIG. 10 is a diagram showing the operation of the cell culture apparatus in a case of carrying out the culture medium exchange process according to an embodiment of the disclosed technology.

FIG. 10 is a diagram showing an operation of the cell culture apparatus 100 in a case of carrying out the process carried out in step S9 shown in FIG. 2, that is, culture medium exchange [4]. In FIG. 10, the order of supplying the processing targets (cell suspension, culture medium, additive, and a mixture thereof) to the respective processing units is shown.

In step I1, the control unit 80 controls the on-off valve V12 in an open state and drives a predetermined pump. As a result, the cell suspension containing the spent culture medium is transferred from the culture vessel 70 to the cell supply unit 11 through the flow channel F5.

In step I2, the control unit 80 controls the on-off valves V1 and V4 in an open state and drives a predetermined pump. As a result, the cell suspension containing the spent culture medium is transferred from the cell supply unit 11 to the storage container 20 through the flow channel F1, and a fresh culture medium is supplied from the culture medium supply unit 14 to the storage container 20.

In step I3, the control unit 80 controls the on-off valves V5 and V6 in an open state and drives a predetermined pump. As a result, the cell suspension to which the fresh culture medium has been added is transferred from the storage container 20 to the stirring unit 30 through the flow channel F2. The cell suspension to which the fresh culture medium has been added is stirred and mixed in the stirring unit 30.

In step I4, the control unit 80 controls the on-off valves V7 and V10 in an open state and drives a predetermined pump. As a result, the cell suspension to which the fresh culture medium has been added is supplied from the stirring unit 30 to the third filter unit 53 of the separation unit 50 through the flow channel F3. The cell suspension to which the fresh culture medium has been added is subjected to a membrane separation process in the third filter unit 53, and a part of the mixture containing the spent culture medium and the fresh culture medium is removed together with the intermediates (ectoderm, mesoderm, and endoderm), the undifferentiated cells, and the dead cells. The intermediates, the undifferentiated cells, and the dead cells that have permeated the filter membrane of the third filter unit 53 are recovered in the recovery container 62.

In step I5, the control unit 80 controls the on-off valve V11 in an open state and drives a predetermined pump. As a result, the cell suspension subjected to the membrane separation process is supplied from the third filter unit 53 to the culture vessel 70 through the flow channel F4, and therefore the culture medium exchange process is completed.

As described above, the cell culture apparatus 100 has the processing units (the stirring unit 30 and the separation unit 50), the culture vessel 70, and the cell supply unit 11 provided in the middle of the annular flow channel F0 forming a circulation route. In addition, the first additive supply unit 12 and the second additive supply unit 13 for supplying additives necessary for the induction of differentiation and the culture medium supply unit 14 for supplying a fresh culture medium are connected to the annular flow channel F0 forming a circulation route. In addition, the cell culture apparatus 100 has the control unit 80 that controls the feeding of liquid through the flow channels provided in the cell culture apparatus 100. According to the cell culture apparatus 100 having the foregoing configuration, it is possible to continuously carry out a series of processes required for the induction of differentiation of pluripotent stem cells in a closed system.

Further, according to the cell culture apparatus 100 according to the present embodiment, the separation unit 50 is configured to include the first filter unit 51, the second filter unit 52, and the third filter unit 53, each of which comprises a filter membrane in which the sizes of the openings are different from one another. The first filter unit 51, the second filter unit 52, and the third filter unit 53 are selectively used at a predetermined timing during the culture period. This makes it possible to properly separate dead cells, undifferentiated cells, intermediates, and differentiated cells, which are generated during the culture period, from one another.

In addition, according to the cell culture apparatus 100 according to the present embodiment, in a case of adding or re-adding an additive, the control unit 80 carries out control of the feeding of liquid for applying a shear stress to the mixture of the additive and the fresh culture medium, and then combining the cell suspension and the above mixture and transferring the combined mixture to the stirring unit 30. That is, after the viscosity of the mixture containing an additive and a fresh culture medium is brought close to the viscosity of the cell suspension, the above mixture and cell suspension are mixed. This makes it possible to obtain a satisfactory mixing state in a case of mixing a mixture containing the cell suspension, the additive, and the fresh culture medium.

In the present embodiment, a case where the separation unit 50 has three types of filter units, the first filter unit 51, the second filter unit 52, and the third filter unit 53 has been illustrated, but the present invention is not limited to this aspect. The separation unit 50 may include at least one of the first filter unit 51, the second filter unit 52, or the third filter unit 53.

In addition, in the present embodiment, a filter unit which carries out a membrane separation process has been illustrated as separation means by the separation unit 50, but the present invention is not limited to this aspect. As the separation means by the separation unit 50, centrifugal separation means, vibration separation means, electrolytic separation means, or magnetic separation means can also be used in place of or in combination with the membrane separation means.

In addition, in the present embodiment, although a case where the cell culture apparatus 100 comprises the storage container 20 has been illustrated, it is also possible to omit the storage container 20. In a case where the storage container 20 is omitted, the pipe forming a flow channel may be made to function as the storage container.

Second Embodiment

Figure 11:
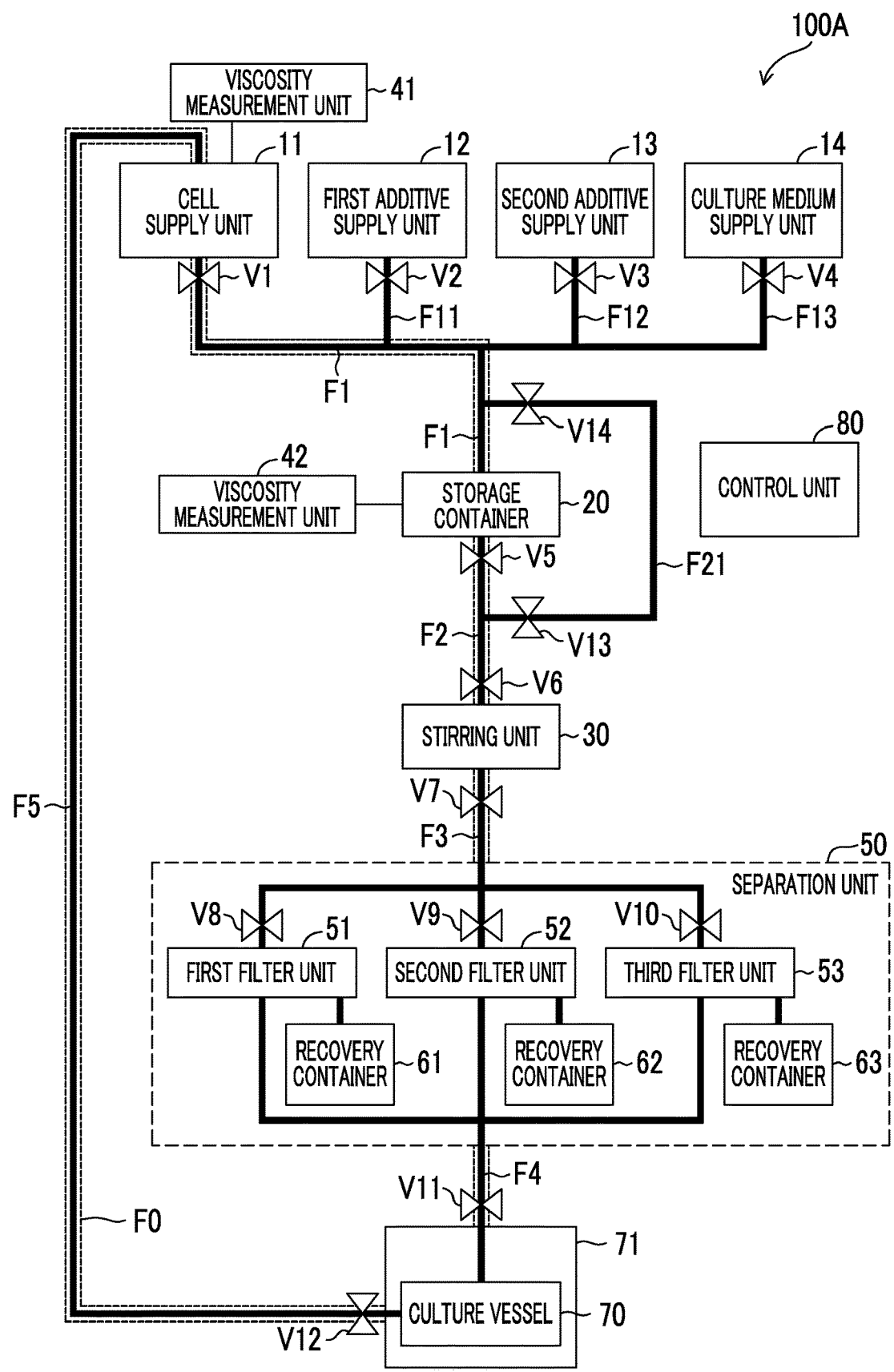
FIG. 11 is a block diagram showing a configuration of a cell culture apparatus according to another embodiment of the disclosed technology.

FIG. 11 is a block diagram showing a configuration of a cell culture apparatus 100 A according to a second embodiment of the disclosed technology. In the cell culture apparatus 100 according to the first embodiment, a case where a mixture containing an additive and a fresh culture medium is circulated between the storage container 20 and the stirring unit 30 in order to apply a shear stress to the mixture has been illustrated. The cell culture apparatus 100A according to the second embodiment differs from the cell culture apparatus 100 according to the first embodiment in terms of a liquid feeding path for applying a shear stress to the mixture of an additive and a fresh culture medium.

The cell culture apparatus 100 A according to the second embodiment has a flow channel F21 connecting the outlet and the inlet of the storage container 20 as the liquid feeding path for applying a shear stress to the mixture of an additive and a fresh culture medium. The control unit 80 applies a shear stress to a mixture containing an additive and a fresh culture medium by allowing the mixture to flow into the pipe constituting the flow channel F21, and then combines a cell suspension and the above mixture in the storage container 20 and transfers the combined mixture to the stirring unit 30.

Specifically, the control unit 80 controls the on-off valves V5, V13, and V14 in an open state and drives a predetermined pump in a state in which the mixture containing an additive and a fresh culture medium is accommodated in the storage container 20. As a result, the mixture containing an additive and a fresh culture medium accommodated in the storage container 20 flows out from the storage container 20 and then returns to the storage container 20 through the flow channel F21. While the mixture containing an additive and a fresh culture medium flows into the flow channel F21, a shear stress is applied to the mixture by the friction with the wall surface in the pipe constituting the flow channel F21, and the viscosity of the mixture is decreased.

The viscosity of the mixture containing an additive and a fresh culture medium accommodated in the storage container 20 is measured by the viscosity measurement unit 42, and the measurement results are notified to the control unit 80. The control unit 80 carries out continuously the feeding of liquid which circulates the mixture through the flow channel F21 until the difference value between the viscosity of the mixture notified from the viscosity measurement unit 42 and the viscosity of the cell suspension notified from the viscosity measurement unit 41 becomes equal to or less than a predetermined value. In addition, the control unit 80 may continuously carry out the feeding of liquid which circulates the mixture through the flow channel F21 until the value of the viscosity of the mixture notified from the viscosity measurement unit 42 becomes equal to or less than a predetermined value. In addition, the control unit 80 may continuously carry out the feeding of liquid which circulates the mixture through the flow channel F21 until the number of processing cycles reaches a predetermined number of cycles.

In a case where the feeding of liquid for applying a shear stress to the mixture containing an additive and a fresh culture medium is completed, the control unit 80 controls the on-off valves V5, V13, and V14 in a closed state and controls the on-off valve V1 in an open state, and drives a predetermined pump. As a result, the cell suspension accommodated in the cell supply unit 11 is transferred to the storage container 20 through the flow channel F1, and is then combined with the mixture containing the first additive and the fresh culture medium whose viscosity has been adjusted.

Thereafter, the control unit 80 controls the on-off valves V5 and V6 in an open state and drives a predetermined pump. As a result, a mixture containing the cell suspension, the additive, and the fresh culture medium is transferred from the storage container 20 to the stirring unit 30 through the flow channel F2. The mixture containing the cell suspension, the additive, and the fresh culture medium is stirred and mixed in the stirring unit 30. By applying a shear stress to the mixture containing an additive and a fresh culture medium to carry out viscosity adjustment, a satisfactory mixing state can be obtained in the mixture containing the cell suspension, the additive, and the fresh culture medium.

In addition, as a method for applying a shear stress to the mixture containing an additive and a fresh culture medium, it is also possible to use a method in which the storage container 20 is made of a flexible material such as a plastic film, and an external force is applied to the storage container 20 accommodating the mixture containing an additive and a fresh culture medium.

Third Embodiment

In the cell culture apparatus according to the embodiment of the disclosed technology, the temperature T1 inside the incubator 71 is kept constant at, for example, 37° C., and the temperature T2 outside the incubator 71 is room temperature (for example 25° C.). Therefore, in a case where the cell suspension is made to flow into the culture vessel 70 accommodated inside the incubator 71 and in a case where the cell suspension is made to flow out of the incubator 71, the cells are subjected to heat shock due to a temperature difference of 12° C. The heat shock may damage the cells.

Figure 12:
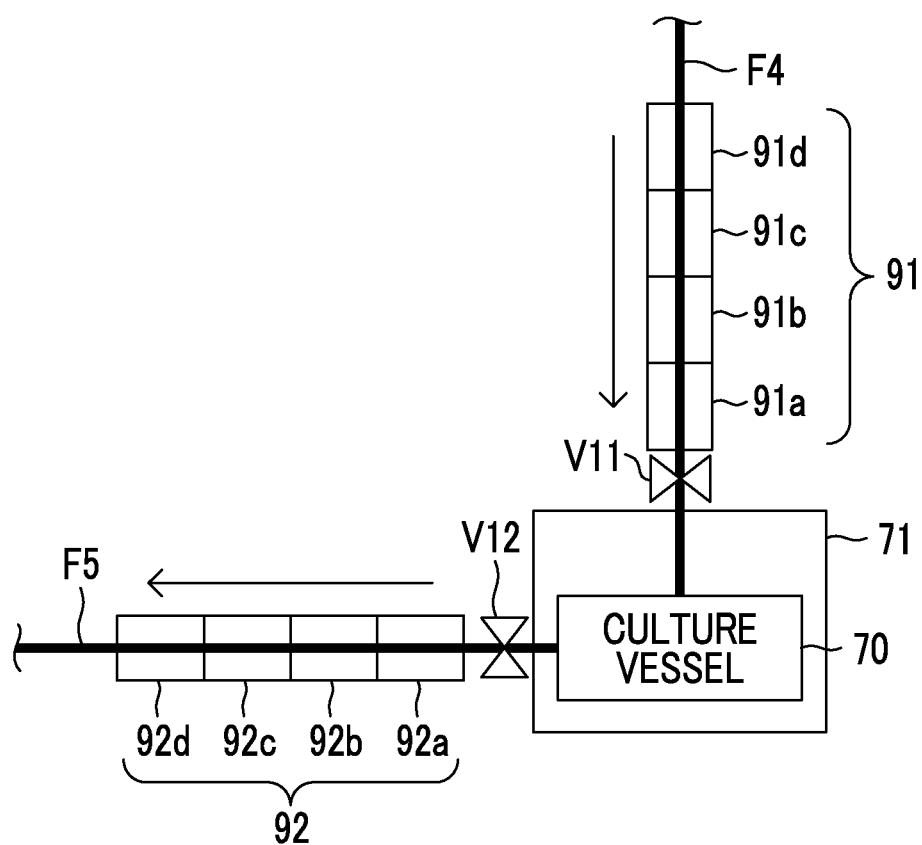
FIG. 12 is a diagram showing a partial configuration of a cell culture apparatus according to another embodiment of the disclosed technology.

FIG. 12 is a diagram showing a partial configuration of a cell culture apparatus according to a third embodiment of the disclosed technology. The cell culture apparatus according to the third embodiment comprises temperature gradient-reducing mechanisms 91 and 92 for reducing the temperature gradient between the inside and the outside of the incubator 71 accommodating the culture vessel 70.

The temperature gradient-reducing mechanism 91 is configured to include a plurality of heating units $91a$, $91b$, $91c$, and $91d$. The heating units $91a$, $91b$, $91c$, and $91d$ are provided in the flow channel F4 through which the cell suspension flowing into the culture vessel 70 accommodated in the incubator 71 passes. The heating units $91a$, $91b$, $91c$, and $91d$ can independently set heating temperatures, and heat the cell suspension flowing in the flow channel F4 at temperatures different from one another. Assuming that the set temperatures of the heating units $91a$, $91b$, $91c$, and $91d$ are T1$a$, T1$b$, T1$c$, and T1$d$, respectively, the temperature setting of each heating unit is carried out such that T2 (25° C.)<T1$d$<T1$c$<T1$b$<T1$a$<T1 (37° C.). As a result, the temperature of the cell suspension flowing in the flow channel F4 gradually increases toward the temperature T1 (37° C.) inside the incubator 71. That is, the temperature gradient-reducing mechanism 91 reduces the temperature gradient which is the temperature change per hour of the cell suspension due to the temperature difference between the inside and the outside of the incubator 71. The temperature gradient is preferably, for example, 0.1 (° C./s) or less. In the present embodiment, a case where the temperature gradient-reducing mechanism 91 is configured by the four heating units $91a$, $91b$, $91c$, and $91d$ has been exemplified, but the number of heating units may be appropriately increased or decreased so as to realize a desired temperature gradient.

On the other hand, the temperature gradient-reducing mechanism 92 is configured to include a plurality of cooling units $92a$, $92b$, $92c$, and $92d$. The cooling units $92a$, $92b$, $92c$, and $92d$ are provided in the flow channel F5 through which the cell suspension flowing out of the culture vessel 70 accommodated in the incubator 71 passes. The cooling units $92a$, $92b$, $92c$, and $92d$ can set cooling temperatures independently of one another, and cool the cell suspension flowing in the flow channel F5 at temperatures different from one another. Assuming that the set temperatures of the cooling units $92a$, $92b$, $92c$, and $92d$ are T2$a$, T2$b$, T2$c$, and T2$d$, respectively, the temperature setting of each cooling unit is carried out such that T2 (25° C.)<T2$d$<T2$c$<T2$b$<T2$a$<T1 (37° C.). As a result, the temperature of the cell suspension flowing in the flow channel F5 gradually decreases toward the temperature T2 (25° C.) outside the incubator 71. That is, the temperature gradient-reducing mechanism 92 reduces the temperature gradient which is the temperature change per hour of the cell suspension due to the temperature difference between the inside and the outside of the incubator 71. The temperature gradient is preferably, for example, 0.1 (° C./s) or less. In the present embodiment, a case where the temperature gradient-reducing mechanism 92 is configured by the four cooling units $92a$, $92b$, $92c$, and $92d$ has been exemplified, but the number of cooling units may be appropriately increased or decreased so as to realize a desired temperature gradient.

As described above, according to the cell culture apparatus according to the third embodiment of the disclosed technology, the temperature gradient of the temperature change of the cell suspension due to the temperature difference between the inside and the outside of the incubator 71 is reduced by the temperature gradient-reducing mechanisms 91 and 92. This makes it possible to reduce or eliminate the damage to the cells caused by the temperature difference between the inside and the outside of the incubator 71.

Fourth Embodiment

Figure 13:
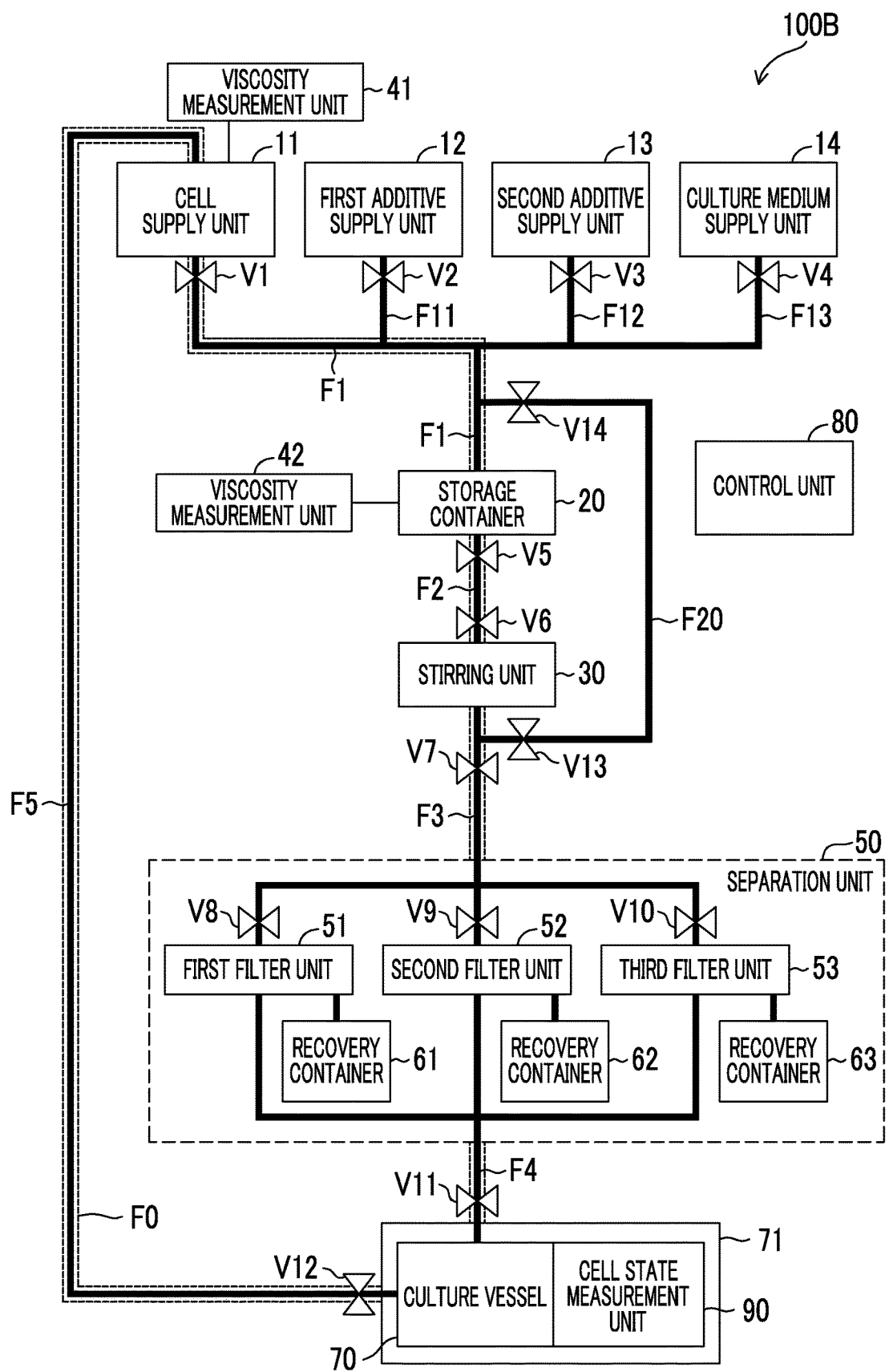
FIG. 13 is a block diagram showing a configuration of a cell culture apparatus according to another embodiment of the disclosed technology.

FIG. 13 is a diagram showing a configuration of a cell culture apparatus 100B according to a fourth embodiment of the disclosed technology. The cell culture apparatus 100B according to the fourth embodiment further has a cell state measurement unit 90. The cell state measurement unit 90 comprises a camera for imaging the cells accommodated in the culture vessel 70, and supplies the image obtained by imaging to the control unit 80.

The control unit 80 detects the state of the cells accommodated in the culture vessel 70 from the image supplied from the cell state measurement unit 90. The control unit 80 determines whether or not to shift to each processing step shown in FIG. 2, based on the state of the cells detected from the image.

As described above, it is possible to carry out each processing required for the induction of differentiation at an appropriate timing and it is possible to increase the productivity of differentiated cells, by determining whether or not to shift to each processing step based on the image of the cells accommodated in the culture vessel 70.

The disclosure of JP2017-008911 filed on Jan. 20, 2017 is incorporated herein by reference in its entirety. In addition, all documents, patent applications, and technical standards described in the present specification are incorporated herein by reference to the same extent as the case where each individual document, patent application, and technical standard were specifically and individually indicated to be incorporated by reference.

What is claimed is:
1. A cell culture apparatus comprising:
a cell supply unit that supplies cells;
a culture medium supply unit that supplies a culture medium;
an additive supply unit that supplies an additive for inducing the differentiation of undifferentiated cells;
a stirring unit that stirs a processing target;

a separation unit that separates a component contained in the processing target;

a culture vessel that cultures the cells;

a first flow channel that forms a circulation route passing through the cell supply unit, the stirring unit, the separation unit, and the culture vessel, and that returns from the culture vessel to the cell supply unit;

a second flow channel that connects the culture medium supply unit and the first flow channel;

a third flow channel that connects the additive supply unit and the first flow channel; and a control unit that controls the feeding of liquid through the first flow channel, the second flow channel, and the third flow channel.

2. The cell culture apparatus according to claim 1, wherein the separation unit has at least one of a first filter membrane that carries out membrane separation of the undifferentiated cells from dead cells; a second filter membrane that carries out membrane separation of intermediates prior to the differentiation of the undifferentiated cells into differentiated cells from the undifferentiated cells; or a third filter membrane that carries out membrane separation of the intermediates from the differentiated cells.

3. The cell culture apparatus according to claim 2, wherein the separation unit has a plurality of filter membranes including at least two of the first filter membrane, the second filter membrane, and the third filter membrane, and the control unit carries out control of selectively passing a cell suspension containing the cells through any of the plurality of filter membranes.

4. The cell culture apparatus according to claim 2, wherein sizes of openings provided in the membrane surfaces of the first filter membrane, the second filter membrane, and the third filter membrane are different from one another.

5. The cell culture apparatus according to claim 1, wherein the control unit carries out control of the feeding of liquid for applying a shear stress to a mixture of the additive and the culture medium, and then combining a cell suspension containing the cells and the mixture and transferring the combined mixture to the stirring unit.

6. The cell culture apparatus according to claim 5, further comprising:

a storage container provided between the cell supply unit and the stirring unit in the middle of the first flow channel, wherein the control unit carries out control of circulating the mixture between the storage container and the stirring unit to apply a shear stress to the mixture, and then combining the cell suspension and the mixture in the storage container and transferring the combined mixture to the stirring unit.

7. The cell culture apparatus according to claim 5, further comprising:

a storage container provided between the cell supply unit and the stirring unit in the middle of the first flow channel, wherein the control unit carries out control of flowing the mixture into a pipe to apply a shear stress to the mixture, and then combining the cell suspension and the mixture in the storage container and transferring the combined mixture to the stirring unit.

8. The cell culture apparatus according to claim 5, wherein the control unit continuously carries out the feeding of liquid for applying a shear stress to the mixture until the viscosity of the mixture reaches a predetermined viscosity.

9. The cell culture apparatus according to claim 1, wherein the additive supply unit includes a first additive supply unit that supplies a first additive containing a Wnt signaling activator, and a second additive supply unit that supplies a second additive containing a Wnt signaling inhibitor.

10. The cell culture apparatus according to claim 1, further comprising:

an incubator that accommodates the culture vessel and keeps an ambient temperature of the culture vessel constant; and a temperature gradient-reducing mechanism that reduces a temperature gradient generated along the first flow channel due to a temperature difference between the inside and the outside of the incubator.

11. The cell culture apparatus according to claim 1, wherein the separation unit comprises a plurality of filter membranes, and the control unit is configured to selectively feed the liquid through any one of the plurality of filter membranes.

12. The cell culture apparatus according to claim 11, wherein the separation unit comprises at least two of: a first filter membrane that carries out membrane separation of the undifferentiated cells from dead cells; a second filter membrane that carries out membrane separation of intermediates prior to the differentiation of the undifferentiated cells into differentiated cells from the undifferentiated cells; or a third filter membrane that carries out membrane separation of the intermediates from the differentiated cells.

13. A cell culture method for culturing a cell using the cell culture apparatus according to claim 1, wherein the control unit carries out control of transferring a mixture containing the cell supplied from the culture medium supply unit, the additive supplied from the additive supply unit, and the culture medium supplied from the culture medium supply unit to the culture vessel through the stirring unit and the separation unit.

* * * * *